(12) United States Patent
Jablons et al.

(10) Patent No.: US 11,932,606 B2
(45) Date of Patent: Mar. 19, 2024

(54) ANTI-CANCER/ANTI-FIBROSIS COMPOUNDS

(71) Applicants: THE REGENTS OF THE UNIVERSITY OF CALIFORNIA, Oakland, CA (US); METKINE THERAPEUTICS, INC., Alameda, CA (US)

(72) Inventors: David M. Jablons, San Francisco, CA (US); Wei Xu, San Francisco, CA (US); Liang You, San Francisco, CA (US); Shu Liu, San Francisco, CA (US); Shendong Yuan, Richmond, CA (US); Sunghoon Ma, Richmond, CA (US); Morrison Mac, Richmond, CA (US)

(73) Assignee: The Regents of the University of California, Oakland, CA (US)

( * ) Notice: Subject to any disclaimer, the term of this patent is extended or adjusted under 35 U.S.C. 154(b) by 952 days.

(21) Appl. No.: 16/634,063

(22) PCT Filed: Jul. 31, 2018

(86) PCT No.: PCT/US2018/044663
§ 371 (c)(1),
(2) Date: Jan. 24, 2020

(87) PCT Pub. No.: WO2019/028059
PCT Pub. Date: Feb. 7, 2019

(65) Prior Publication Data
US 2023/0192621 A1 Jun. 22, 2023

Related U.S. Application Data

(60) Provisional application No. 62/539,237, filed on Jul. 31, 2017.

(51) Int. Cl.
*C07D 221/10* (2006.01)
*A61P 35/00* (2006.01)

(52) U.S. Cl.
CPC ............ *C07D 221/10* (2013.01); *A61P 35/00* (2018.01)

(58) Field of Classification Search
CPC .... C07D 221/10; C07D 401/04; A61K 31/47; A61P 35/00
See application file for complete search history.

(56) References Cited

U.S. PATENT DOCUMENTS

| | | | | |
|---|---|---|---|---|
| 5,648,021 A * | 7/1997 | Wingen | ................ | C07C 43/225 544/298 |
| 5,888,422 A * | 3/1999 | Manero | ............... | C07C 17/2632 544/347 |
| 6,171,519 B1 * | 1/2001 | Nonaka | .............. | C09K 19/3466 252/299.61 |

FOREIGN PATENT DOCUMENTS

| WO | WO 2011/035019 | | 3/2011 |
|---|---|---|---|
| WO | 2019028059 | * | 7/2018 |

OTHER PUBLICATIONS

Pubchem CID 65571661 (Year: 2012).*
Pubchem CID 160447 (Year: 2005).*
(Continued)

*Primary Examiner* — Carlos A Azpuru
(74) *Attorney, Agent, or Firm* — Todd Esker; Bozicevic, Field & Francis LLP

(57) ABSTRACT

This invention provides, among other things, compounds useful for treating diseases such as fibrosis and/or cancer, pharmaceutical formulations containing such compounds, as well as combinations of these compounds with at least one additional therapeutic agent.

13 Claims, 7 Drawing Sheets

(56) References Cited

OTHER PUBLICATIONS

European Extended Search Report, dated Nov. 26, 2020, EP Application No. 18840434.7.
Pubchem. CID 69571661. Dec. 1, 2012, pp. 1-10. Retrieved from the Internet <URL: https://pubchem.ncbi.nlm.nih.gov/compound/69571661>; p. 3, formula.
Pubchem. CID 160447. Mar. 27, 2005, pp. 1-16. Retrieved from the Internet <URL: https://pubchem.ncbi.nlm.nih.gov/compound/160447>; p. 3, formula.
PCT International Search and Written Opinion, dated Oct. 1, 2018, PCT/US2018/044663.

* cited by examiner

MV-4-11 treated with compound 29 for 48 hours

MOLM-14 treated with compound 29 (24H)

MOLM-14 xenograft mouse tumor treated with compound 29

Pharmacodynamics study of MOLM-14 xenograft treated with compound 29

ANTI-CANCER/ANTI-FIBROSIS COMPOUNDS

CROSS-REFERENCES TO RELATED APPLICATIONS

This application is a U.S. National Phase application under 35 U.S.C. § 371 of International Application PCT/US18/44663, filed Jul. 31, 2018, which claims priority benefit of U.S. Provisional Application No. 62/539,237 filed Jul. 31, 2017, the disclosure of which is incorporated by reference its entirety.

BACKGROUND OF THE INVENTION

There is a need in the art for compounds which can treat fibrosis and/or cancer. This, and other uses of these compounds, are described herein.

SUMMARY OF THE INVENTION

This invention provides, among other things, compounds useful for treating diseases associated with CDK8 and/or CDK19 and/or HIPK2 and/or CK2a, pharmaceutical formulations containing such compounds, as well as combinations of these compounds with at least one additional therapeutic agent.

DETAILED DESCRIPTION OF THE INVENTION

I. Definitions and Abbreviations

Figure 1A:
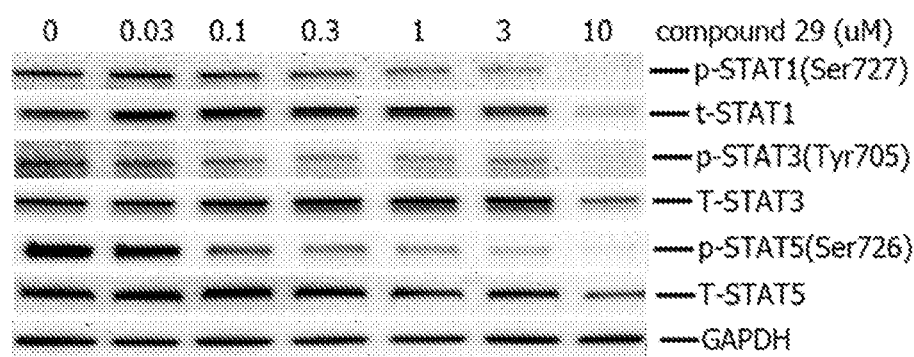
FIG. 1A-FIG. 1E: show Acute Myeloid Leukemia (AML) Data Cell viability method and data (Western Blot). (A) MV-4-11 treated with compound 29 (24H). (B) MV-4-11 treated with compound 29 (48H). (C) MV-4-11 treated with compound 29 for 48 hours. (D) MOLM-14 treated with compound 29 (24H). (E) MOLM-14 treated with compound 29 (48H).

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N-ethylcarbodiimide hydrochloride; ELS is evaporative light scattering; equiv or eq is equivalent; h is hours; HATU is O-(7-azabenzotriazol-1-yl)-N,N,N,N-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis(diphenylphosphino) ferroceneldichloropalladium(II); Pd/C is the catalyst known as palladium on carbon; $Pd_2(dba)_3$ is an organometallic catalyst known as tris(dibenzylideneacetone) dipalladium(O); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

Where substituent groups are specified by their conventional chemical formulae, written from left to right, they equally encompass the chemically identical substituents, which would result from writing the structure from right to left, e.g., —CH₂O— is intended to also recite —OCH₂—.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclobutyl, cyclohexyl, (cyclohexyl)methyl, cyclopropyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH₂CH₂CH₂CH₂—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —O—CH₃, —CH₂—CH₂—O—CH₃, —CH₂—CH₂—NH—CH₃, —CH₂—CH₂—N(CH₃)—CH₃, —CH₂—CH₂—CH₂—N(CH₃)—CH₃, —CH₂—S—CH₂—CH₃, —CH₂—CH₂—S(O)—CH₃, —CH₂—CH₂—S(O)₂—CH₃, —CH=CH—O—CH₃, —CH₂—CH=N—OCH₃, and —CH=CH—N(CH₃)—CH₃. Up to two heteroatoms may be consecutive, such as, for example, —CH₂—NH—OCH₃. Similarly, the term "heteroalkylene" by itself or as part of another substituent means a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 2-(4-methylpiperazin-1-yl)ethyl, 3-(4-methylpiperazin-1-yl)propyl, 2-morpholinoethyl, 3-morpholinopropyl, 1-methylazetidin-3-yl, 1-ethylazetidin-3-yl, 1-isopropylazetidin-3-yl, 1-methylpiperidin-4-yl, 1-ethylpiperidin-4-yl or, 1-isopropylpiperidin-4-yl, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 2-fluoroethyl, 2,2-difluoroethyl, 2-chloroethyl, 3-chloropropyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR""—C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2m'+1), where m' is the total number of carbon atoms in such radical. R', R", R"' and R"" each preferably independently refer to hydrogen, substituted or unsubstituted haloalkyl, substituted or unsubstituted heteroalkyl, substituted or unsubstituted heterocycloalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR""—C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"', R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"', R"" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted C$_1$ or C$_2$ or C$_3$ or C$_4$ or C$_5$ or C$_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5 to 7-membered ring" or "5 or 6 or 7 membered ring" includes, for example phenyl, pyridinyl and piperidinyl. The term "5 to 7-membered heterocycloalkyl ring" "5 or 6 or 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), and aluminum (Al).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host/patient/animal. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host/patient/animal. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from animal to animal, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical formulation administered to an animal via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as CDK8 (Cyclin-Dependent Kinase 8) and/or CDK19 (Cyclin-Dependent Kinase 19) and/or HIPK2 (Homeodomain-Interacting Protein Kinase 2) and/or CK2a (Casein Kinase II alpha).

Embodiments of the invention also encompass compounds that are poly- or multi-valent species, including, for example, species such as dimers, trimers, tetramers and higher homologs of the compounds of use in the invention or reactive analogues thereof.

II. Introduction

The invention provides novel compounds. The novel compounds, as well as pharmaceutical formulations containing such compounds or combinations of these compounds with at least one additional therapeutic agent, can be used for, among other things, treating diseases, including cancer.

III. The Compounds

III. a)
In one aspect, the invention provides a compound of the invention. In an exemplary embodiment, the invention is a compound described herein. In an exemplary embodiment, the invention is a compound according to a formula described herein.

In another aspect, the invention provides a compound, or a salt or a hydrate or a solvate thereof, having a structure according to formula (I):

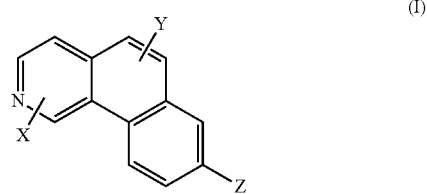

wherein
- Z is —COOR⁵ or —C(O)NHR⁵, wherein R⁵ is H or substituted or unsubstituted alkyl or substituted or unsubstituted cycloalkyl;
- Y is H or halogen or nitro or cyano or substituted or unsubstituted aryl or substituted or unsubstituted heteroaryl or substituted or unsubstituted alkyl or substituted or unsubstituted cycloalkyl or NR$^1$R$^2$, wherein R$^1$ and R$^2$ are each independently selected from H or substituted or unsubstituted alkyl or substituted or unsubstituted cycloalkyl or substituted or unsubstituted heterocycloalkyl or wherein R$^1$ and R$^2$, along with the nitrogen to which they are attached, are optionally joined to form a substituted or unsubstituted 4 to 8 membered ring; and
- X is H or halogen or OR$^3$ or NR$^3$R$^4$, wherein R$^3$ and R$^4$ are each independently selected from H or substituted or unsubstituted alkyl or substituted or unsubstituted cycloalkyl or wherein R$^3$ and R$^4$, along with the nitrogen to which they are attached, are optionally joined to form a substituted or unsubstituted 4 to 8 membered ring.

In another aspect, the invention provides a compound, or a salt or a hydrate or a solvate thereof, having a structure according to formula (II):

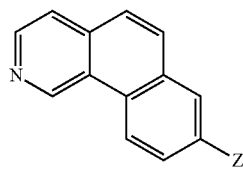

(II)

wherein Z is as described herein. In an exemplary embodiment, the structure is according to formula (II), and Z is —COOR⁵ or —C(O)NHR⁵, wherein R⁵ is substituted or unsubstituted alkyl or substituted or unsubstituted cycloalkyl. In an exemplary embodiment, the structure is according to formula (II), and Z is —COOH or —C(O)NH$_2$.

In another aspect, the invention provides a compound, or a salt or a hydrate or a solvate thereof, having a structure according to formula (Ma) or (IIIb):

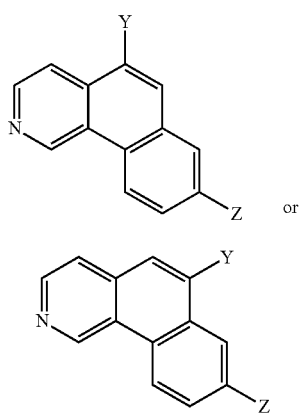

(IIIa)

or (IIIb)

wherein Z is as described herein, and Y is halogen or nitro or cyano or substituted or unsubstituted aryl or substituted or unsubstituted heteroaryl or substituted or unsubstituted alkyl or substituted or unsubstituted cycloalkyl or NR$^1$R$^2$, wherein R$^1$ and R$^2$ are each independently selected from H or substituted or unsubstituted alkyl or substituted or unsubstituted cycloalkyl or wherein R$^1$ and R$^2$, along with the nitrogen to which they are attached, are optionally joined to form a substituted or unsubstituted 4 to 8 membered ring. In an exemplary embodiment, the compound has a structure according to formula (Ma), wherein Z is —COOR⁵ or —C(O)NHR⁵, wherein R⁵ is substituted or unsubstituted alkyl or substituted or unsubstituted cycloalkyl and Y is as described herein. In an exemplary embodiment, the compound has a structure according to formula (IIIb), wherein Z is —COOR⁵ or —C(O)NHR⁵, wherein R⁵ is substituted or unsubstituted alkyl or substituted or unsubstituted cycloalkyl and Y is as described herein. In an exemplary embodiment, the compound has a structure according to formula (Ma), wherein Z is COOH and Y is as described herein. In an exemplary embodiment, the compound has a structure according to formula (IIIb), wherein Z is COOH and Y is as described herein. In an exemplary embodiment, the compound has a structure according to formula (Ma), wherein Z is CONH$_2$ and Y is as described herein. In an exemplary embodiment, the compound has a structure according to formula (IIIb), wherein Z is CONH$_2$ and Y is as described herein.

In another aspect, the invention provides a compound, or a salt or a hydrate or a solvate thereof, having a structure according to formula (IVa) or (IVb):

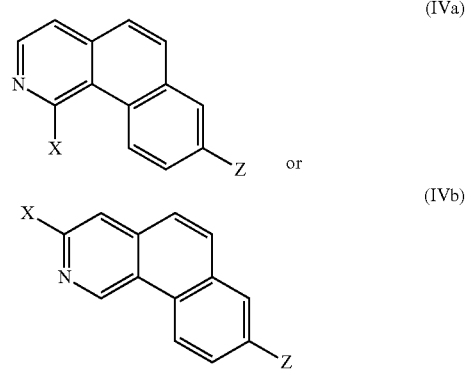

(IVa)

or (IVb)

wherein Z is as described herein and X is halogen or OR$^3$ or NR$^3$R$^4$, wherein R$^3$ and R$^4$ are each independently selected from H or substituted or unsubstituted alkyl or substituted or unsubstituted cycloalkyl or wherein R$^3$ and R$^4$, along with the nitrogen to which they are attached, are optionally joined to form a substituted or unsubstituted 4 to 8 membered ring. In an exemplary embodiment, the compound has a structure according to formula (IVa), wherein Z is —COOR⁵ or —C(O)NHR⁵, wherein R⁵ is substituted or unsubstituted alkyl or substituted or unsubstituted cycloalkyl and X is halogen or OR$^3$ or NR$^3$R$^4$, wherein R$^3$ and R$^4$ are each independently selected from H or substituted or unsubstituted alkyl or substituted or unsubstituted cycloalkyl or wherein R$^3$ and R$^4$, along with the nitrogen to which they are attached, are optionally joined to form a substituted or unsubstituted 4 to 8 membered ring. In an exemplary embodiment, the compound has a structure according to formula (IVb), wherein Z is —COOR⁵ or —C(O)NHR⁵, wherein R⁵ is substituted or unsubstituted alkyl or substituted or unsubstituted cycloalkyl and X is halogen or OR$^3$ or NR$^3$R$^4$, wherein R$^3$ and R$^4$ are each independently selected from H or substituted or unsubstituted alkyl or substituted or unsubstituted cycloalkyl or wherein $R^3$ and $R^4$, along with the nitrogen to which they are attached, are optionally joined to form a substituted or unsubstituted 4 to 8 membered ring. In an exemplary embodiment, the compound has a structure according to formula (IVa), wherein Z is COOH and X is halogen or $OR^3$ or $NR^3R^4$, wherein $R^3$ and $R^4$ are each independently selected from H or substituted or unsubstituted alkyl or substituted or unsubstituted cycloalkyl or wherein $R^3$ and $R^4$, along with the nitrogen to which they are attached, are optionally joined to form a substituted or unsubstituted 4 to 8 membered ring. In an exemplary embodiment, the compound has a structure according to formula (IVb), wherein Z is COOH and X is halogen or $OR^3$ or $NR^3R^4$, wherein $R^3$ and $R^4$ are each independently selected from H or substituted or unsubstituted alkyl or substituted or unsubstituted cycloalkyl or wherein $R^3$ and $R^4$, along with the nitrogen to which they are attached, are optionally joined to form a substituted or unsubstituted 4 to 8 membered ring. In an exemplary embodiment, the compound has a structure according to formula (IVa), wherein Z is $CONH_2$ and X is halogen or $OR^3$ or $NR^3R^4$, wherein $R^3$ and $R^4$ are each independently selected from H or substituted or unsubstituted alkyl or substituted or unsubstituted cycloalkyl or wherein $R^3$ and $R^4$, along with the nitrogen to which they are attached, are optionally joined to form a substituted or unsubstituted 4 to 8 membered ring. In an exemplary embodiment, the compound has a structure according to formula (IVb), wherein Z is $CONH_2$ and X is halogen or $OR^3$ or $NR^3R^4$, wherein $R^3$ and $R^4$ are each independently selected from H or substituted or unsubstituted alkyl or substituted or unsubstituted cycloalkyl or wherein $R^3$ and $R^4$, along with the nitrogen to which they are attached, are optionally joined to form a substituted or unsubstituted 4 to 8 membered ring.

In another aspect, the invention provides a compound, or a salt or a hydrate or a solvate thereof, having a structure according to formula (Va) or (Vb) or (Vc) or (Vd):

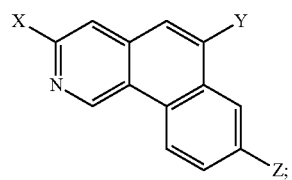

(Vd)

X, Y, and Z are as described herein. In an exemplary embodiment, the compound has a structure according to formula (Va) or (Vb) or (Vc) or (Vd), wherein Z is $—COOR^5$ or $—C(O)NHR^5$, wherein $R^5$ is substituted or unsubstituted alkyl or substituted or unsubstituted cycloalkyl, X is as described herein, and Y is halogen. In an exemplary embodiment, the compound has a structure according to formula (Va) or (Vb) or (Vc) or (Vd), wherein Z is $—COOR^5$ or $—C(O)NHR^5$, wherein $R^5$ is substituted or unsubstituted alkyl or substituted or unsubstituted cycloalkyl, X is as described herein, and Y is Cl. In an exemplary embodiment, the compound has a structure according to formula (Va) or (Vb) or (Vc) or (Vd), wherein Z is $—COOR^5$ or $—C(O)NHR^5$, wherein $R^5$ is substituted or unsubstituted alkyl or substituted or unsubstituted cycloalkyl, X is as described herein, and Y is Br. In an exemplary embodiment, the compound has a structure according to formula (Va) or (Vb) or (Vc) or (Vd), wherein Z is $—COOR^5$ or $—C(O)NHR^5$, wherein $R^5$ is substituted or unsubstituted alkyl or substituted or unsubstituted cycloalkyl, Y is as described herein, and X is $NH_2$. In an exemplary embodiment, the compound has a structure according to formula (Va) or (Vb) or (Vc) or (Vd), wherein Z is $—COOR^5$ or $—C(O)NHR^5$, wherein $R^5$ is substituted or unsubstituted alkyl or substituted or unsubstituted cycloalkyl, Y is $NHR^1$, wherein $R^1$ is as described herein, and X is H or $NH_2$.

In another aspect, the invention provides a compound, or a salt or a hydrate or a solvate thereof, having a structure according to formula (VIa) or (VIb) or (VIc) or (VId):

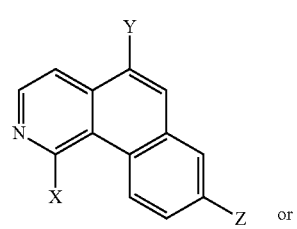

(Va)

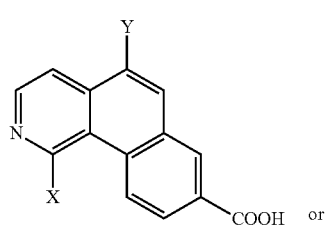

(VIa)

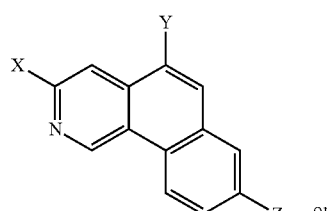

(Vb)

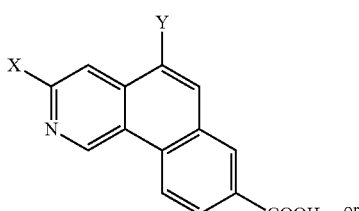

(VIb)

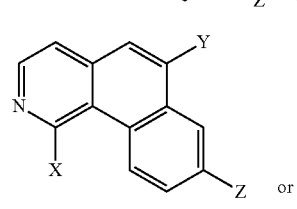

(Vc)

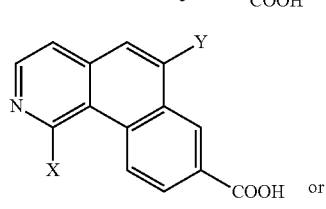

(VIc)

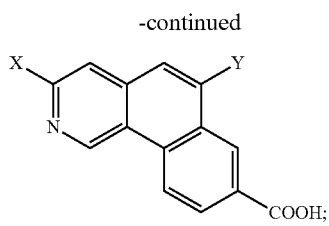
(VId)

wherein Y and X are as described herein. In an exemplary embodiment, the compound has a structure according to formula (VIa) or (VIb) or (VIc) or (VId), wherein X is as described herein, and Y is halogen. In an exemplary embodiment, the compound has a structure according to formula (VIa) or (VIb) or (VIc) or (VId), wherein X is as described herein, and Y is Cl. In an exemplary embodiment, the compound has a structure according to formula (VIa) or (VIb) or (VIc) or (VId), wherein X is as described herein, and Y is Br. In an exemplary embodiment, the compound has a structure according to formula (VIa) or (VIb) or (VIc) or (VId), wherein Y is as described herein, and X is $NH_2$. In an exemplary embodiment, the compound has a structure according to formula (VIa) or (VIb) or (VIc) or (VId), wherein Y is $NHR^1$, wherein IV is as described herein, and X is H or $NH_2$.

In another aspect, the invention provides a compound, or a salt or a hydrate or a solvate thereof, having a structure according to formula (VIIa) or (VIIb) or (VIIc) or (VIId):

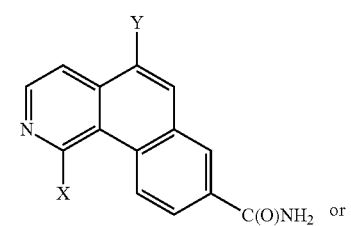
(VIIa)

or

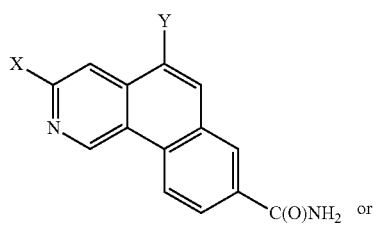
(VIIb)

or

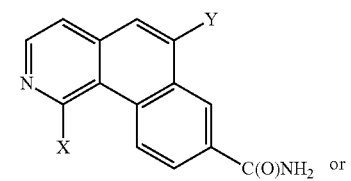
(VIIc)

or

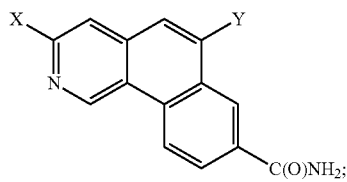
(VIId)

wherein Y and X are as described herein. In an exemplary embodiment, the compound has a structure according to formula (VIIa) or (VIIb) or (VIIc) or (VIId), wherein X is as described herein, and Y is halogen. In an exemplary embodiment, the compound has a structure according to formula (VIIa) or (VIIb) or (VIIc) or (VIId), wherein X is as described herein, and Y is Cl. In an exemplary embodiment, the compound has a structure according to formula (VIIa) or (VIIb) or (VIIc) or (VIId), wherein X is as described herein, and Y is Br. In an exemplary embodiment, the compound has a structure according to formula (VIIa) or (VIIb) or (VIIc) or (VIId), wherein Y is as described herein, and X is $NH_2$. In an exemplary embodiment, the compound has a structure according to formula (VIIa) or (VIIb) or (VIIc) or (VIId), wherein Y is $NHR^1$, wherein $R^1$ is as described herein, and X is H or $NH_2$.

In an exemplary embodiment, the compound has a structure according to formula (I) or (IIIa) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z and X (when listed as a variable) are as described herein, and Y is Br or Cl or CN or $NO_2$. In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z and X (when listed as a variable) are as described herein, and Y is unsubstituted $C_1$ or $C_2$ or $C_3$ or $C_4$ alkyl or p-halophenyl- or m-halophenyl or o-halophenyl or pyridinyl or aminopyridinyl or pyrazolyl. In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z and X (when listed as a variable) are as described herein, and Y is methyl or phenyl or p-chlorophenyl or cyclopropyl or pyridin-3-yl or 6-amino pyridin-3-yl or pyridin-4-yl or pyrazol-3-yl.

In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z and X (when listed as a variable) are as described herein, and Y is $NR^1R^2$, wherein $R^1$ and $R^2$ each independently selected from H or unsubstituted $C_1$ or $C_2$ or $C_3$ or $C_4$ or $C_5$ alkyl or unsubstituted $C_3$-$C_7$ cycloalkyl or unsubstituted $C_3$-$C_7$ heterocycloalkyl or halosubstituted aryl or pyridinyl. In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z and X (when listed as a variable) are as described herein, and Y is $NR^1R^2$, wherein $R^1$ and $R^2$ are each independently selected from H or propyl or sec-butyl or cyclopropyl or cyclobutyl or cyclopentyl or p-halophenyl- or m-halophenyl or o-halophenyl.

In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z and X (when listed as a variable) are as described herein, and Y is $NHR^1$, wherein $R^1$ is H or propyl or sec-butyl or cyclopropyl or cyclobutyl or cyclopentyl or p-chlorophenyl- or m-chlorophenyl.

In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z and X (when listed as a variable) are as described herein, and Y is NR¹R², wherein R¹ and R², along with the nitrogen to which they are attached, are joined to form a substituted or unsubstituted 5 or 6 membered ring. In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z and X (when listed as a variable) are as described herein, and Y is NR¹R², wherein R¹ and R², along with the nitrogen to which they are attached, are joined to form aminopiperidine or piperidine.

In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z is —COOH, X is as described herein, and Y is halogen or cyano or nitro or methyl or phenyl or halogen substituted phenyl or cyclopropyl or piperidine or amino substituted piperidine or pyridinyl or pyrazole or NHR¹, wherein R¹ as described herein. In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z is —CONH₂, X is as described herein, and Y is halogen or cyano or nitro or methyl or phenyl or halogen substituted phenyl or cyclopropyl or piperidine or amino substituted piperidine or pyridinyl or pyrazole or NHR¹, wherein R¹ as described herein.

In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z is —COOH, X is H or NH₂, and Y is halogen or cyano or nitro or methyl or phenyl or halogen substituted phenyl or cyclopropyl or piperidine or amino substituted piperidine or pyridinyl or pyrazole. In an exemplary embodiment, the compound has a structure according to formula (I) or (IIIa) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein Z is —CONH₂, X is H or NH₂, and Y is halogen or cyano or nitro or methyl or phenyl or halogen substituted phenyl or cyclopropyl or piperidine or amino substituted piperidine or pyridinyl or pyrazole.

In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein X is H or NH₂, and Y is halogen or cyano or nitro or methyl or phenyl or halogen substituted phenyl or cyclopropyl or piperidine or amino substituted piperidine or pyridinyl or pyrazole. In an exemplary embodiment, the compound has a structure according to formula (I) or (Ma) or (IIIb) or (IVa) or (IVb) or (IVc) or (IVd) or (Va) or (Vb) or (Vc) or (Vd) or (VIa) or (VIb) or (VIc) or (VId) or (VIIa) or (VIIb) or (VIIc) or (VIId), wherein X is H or NH₂, and Y is NHR¹, wherein R¹ is:

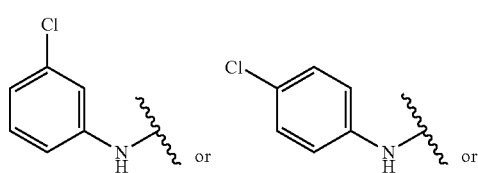

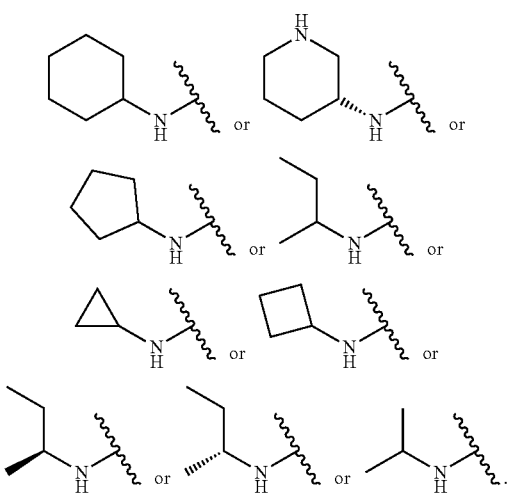

In an exemplary embodiment, the compound is

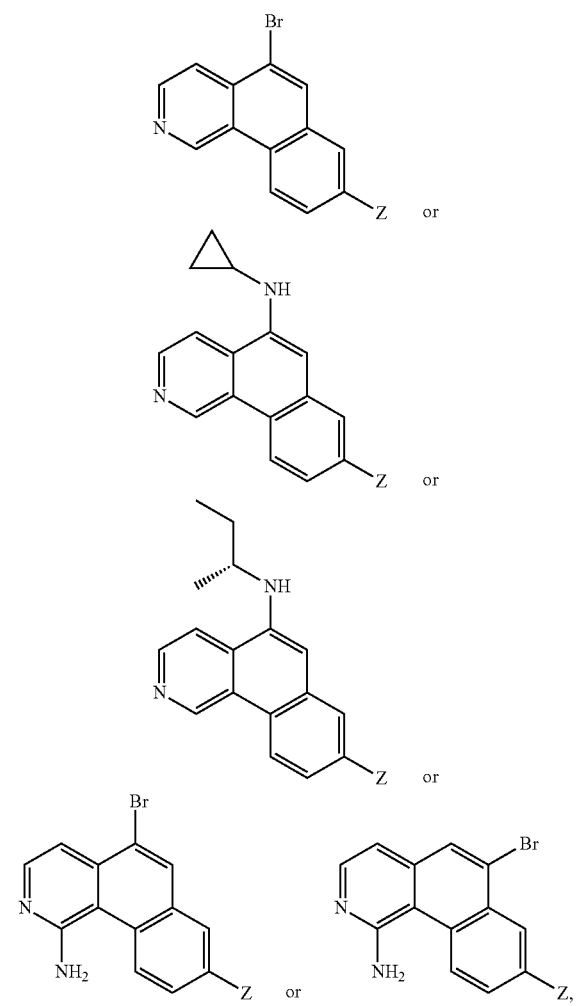

wherein Z is —COOR⁵ or —C(O)NHR⁵, wherein R⁵ is substituted or unsubstituted alkyl or substituted or unsubstituted cycloalkyl.

In an exemplary embodiment, the compound is
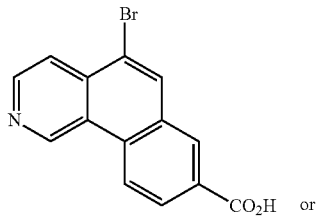
or
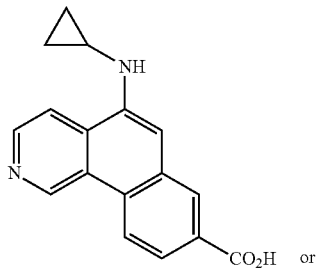
or
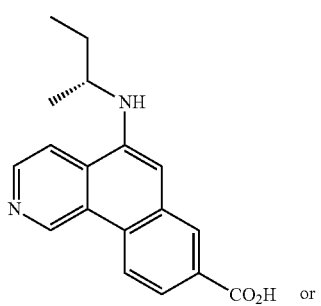
or
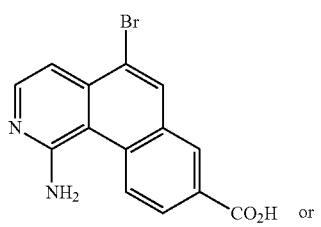
or
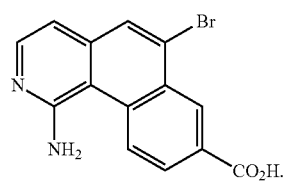
In an exemplary embodiment, the compound is
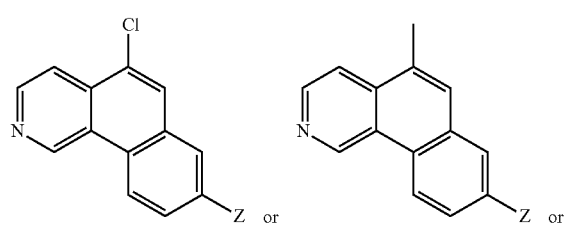
or
-continued
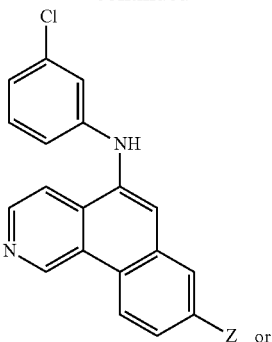
or
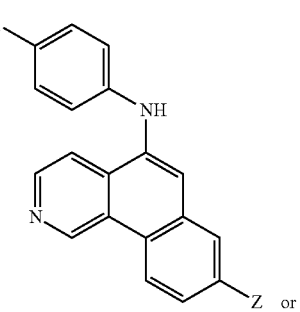
or
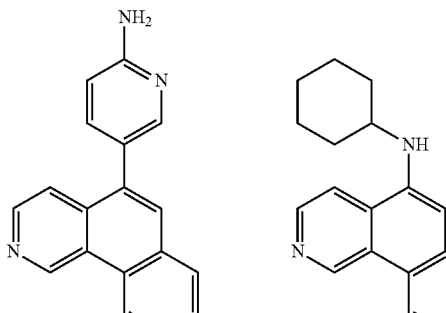
or
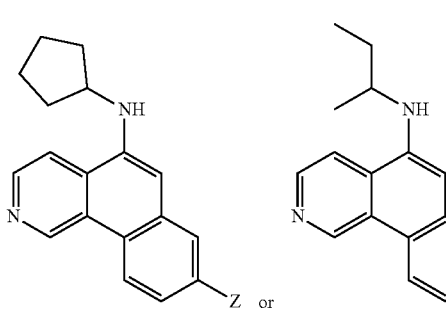
or
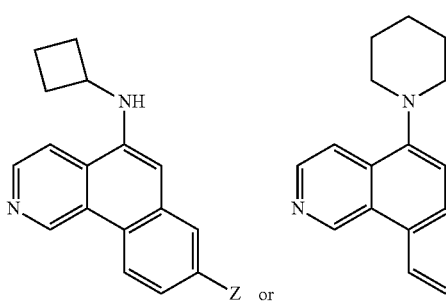
or

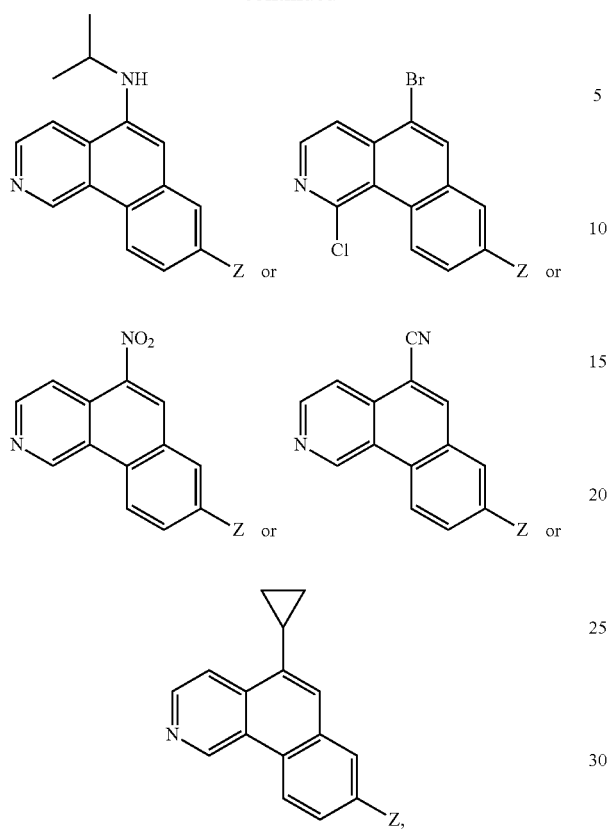
wherein Z is —COOR[5] or —C(O)NHR[5], wherein R[5] is substituted or unsubstituted alkyl or substituted or unsubstituted cycloalkyl.
In an exemplary embodiment, the compound is
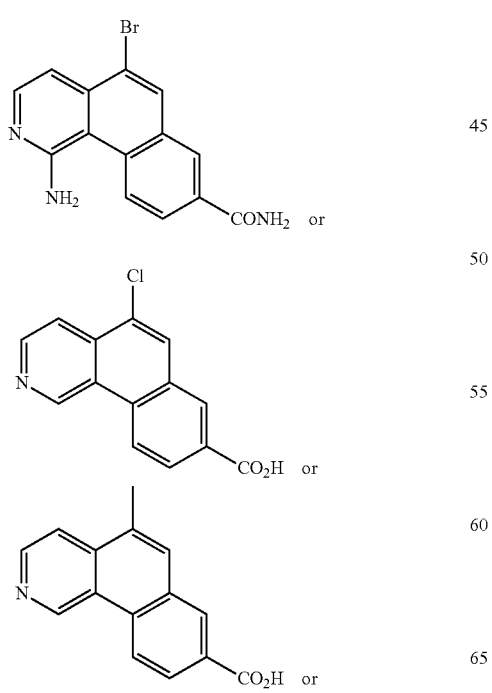
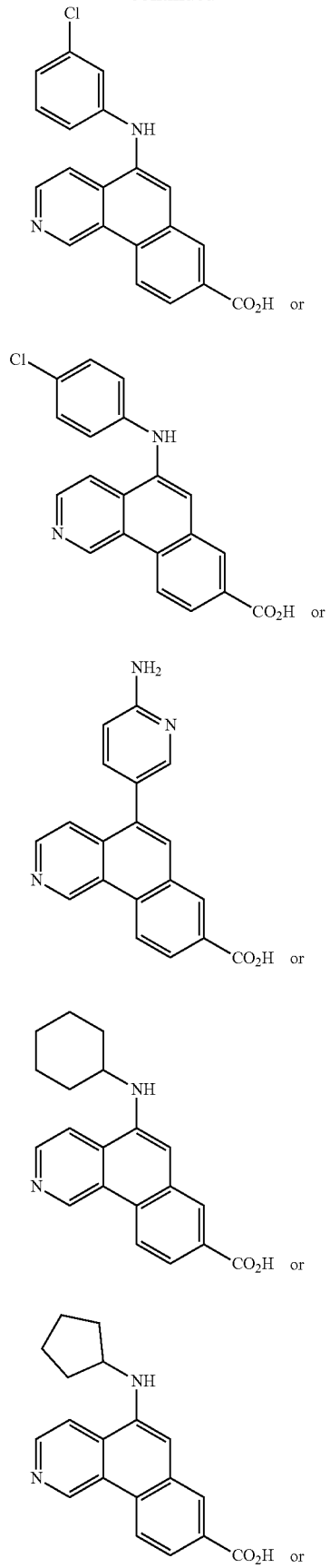

-continued

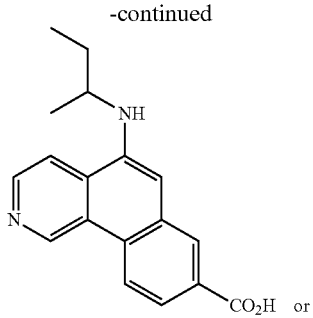

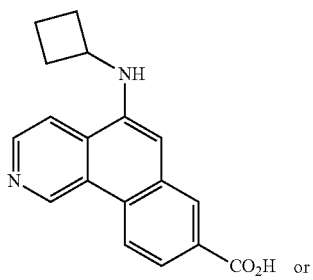

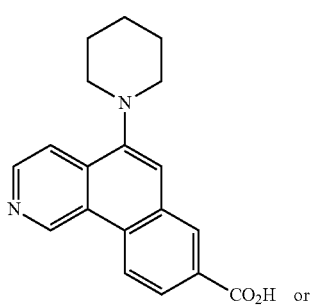

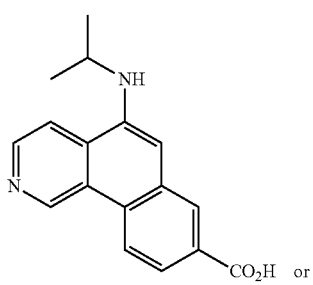

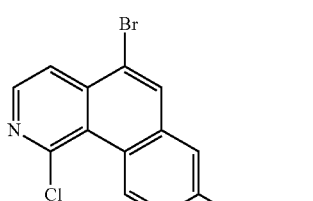

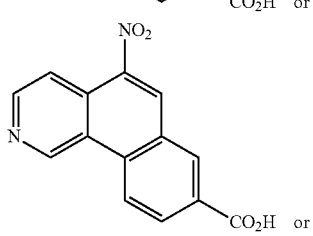

-continued

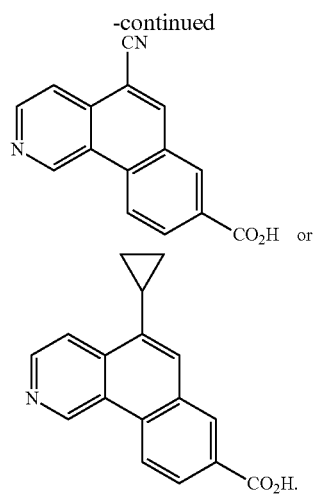

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

III.b) Combinations Comprising Additional Therapeutic Agents

The compounds of the invention may also be used in combination with additional therapeutic agents. The invention thus provides, in a further aspect, a combination comprising a compound of the invention together with at least one additional therapeutic agent, or a salt, hydrate or solvate thereof. In an exemplary embodiment, the combination comprises a compound described herein or a pharmaceutically acceptable salt thereof together with at least one additional therapeutic agent, or a salt, hydrate or solvate thereof. In an exemplary embodiment, the additional therapeutic agent is a compound of the invention. In an exemplary embodiment, the combination comprises: a) a compound of the invention and b) a first additional therapeutic agent, or a salt, hydrate or solvate thereof. In an exemplary embodiment, the combination comprises: a) a compound of the invention; b) a first additional therapeutic agent, or a salt, hydrate or solvate thereof; and c) a second additional therapeutic agent, or a salt, hydrate or solvate thereof. In an exemplary embodiment, the combination comprises: a) a compound of the invention; b) a first additional therapeutic agent, or a salt, hydrate or solvate thereof; c) a second additional therapeutic agent, or a salt, hydrate or solvate thereof; and d) a third additional therapeutic agent, or a salt, hydrate or solvate thereof. In an exemplary embodiment, the combination comprises: a) a compound of the invention according to a formula provided herein and b) a first additional therapeutic agent, or a salt, hydrate or solvate thereof. In an exemplary embodiment, the combination comprises: a) a compound of the invention according to a formula provided herein; b) a first additional therapeutic agent, or a salt, hydrate or solvate thereof; and c) a second additional therapeutic agent, or a salt, hydrate or solvate thereof.

In an exemplary embodiment, an additional therapeutic agent, or a salt, hydrate or solvate thereof is a chemotherapeutic and/or radiation treatment. In an exemplary embodiment, an additional therapeutic agent is a glycolysis inhibitor, or a salt, hydrate or solvate thereof. In an exemplary embodiment, an additional therapeutic agent is a glycolysis inhibitor, which is a glucose analog, or a salt, hydrate or solvate thereof. In an exemplary embodiment, an additional therapeutic agent is a glycolysis inhibitor, which is 2-deoxy-D-glucose (2DG), or a salt, hydrate or solvate thereof.

When a compound of the invention is used in combination with at least one additional therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the animal and will be ultimately at the discretion of the attendant physician.

In an exemplary embodiment, the additional therapeutic agent is useful in treating cancer.

In an exemplary embodiment, the invention is a compound of the invention and 2-deoxy-D-glucose (2DG), or a salt, hydrate or solvate thereof.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the animal ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

It is to be understood that the invention covers all combinations of aspects and/or embodiments, as well as suitable, convenient and preferred groups described herein.

Compounds described herein can be converted into hydrates and solvates by methods similar to those described herein.

IV. Methods of Inhibiting CDK8 and/or CDK19 and/or HIPK2 and/or CK2a

The compounds of the invention inhibit one or more proteins, and said one or more proteins are CDK8 and/or CDK19 and/or HIPK2 and/or CK2a, and therefore have the potential to treat diseases in which these proteins are associated. The compounds of the invention inhibit CDK8, and therefore have the potential to treat diseases in which CDK8 is associated. The compounds of the invention inhibit CDK19, and therefore have the potential to treat diseases in which CDK19 is associated. The compounds of the invention inhibit HIPK2, and therefore have the potential to treat diseases in which HIPK2 is associated. The compounds of the invention inhibit CK2a, and therefore have the potential to treat diseases in which CK2a is associated. In an exemplary embodiment, the compounds of the invention inhibit one or more proteins, and said one or more proteins are CDK8 and/or CDK19 and/or HIPK2 and/or CK2a, and therefore have the potential to treat diseases in which these proteins are associated.

In a further aspect, the invention provides a method of inhibiting CDK8, said method comprising: contacting said CDK8 with an effective amount of a compound of the invention, thereby inhibiting said CDK8. In a further aspect, the invention provides a method of inhibiting CDK19, said method comprising: contacting said CDK19 with an effective amount of a compound of the invention, thereby inhibiting said CDK19. In a further aspect, the invention provides a method of inhibiting HIPK2, said method comprising: contacting said HIPK2 with an effective amount of a compound of the invention, thereby inhibiting said HIPK2. In a further aspect, the invention provides a method of inhibiting CK2a, said method comprising: contacting said CK2a with an effective amount of a compound of the invention, thereby inhibiting said CK2a.

V. Methods of Treating Disease

The compounds of the invention exhibit potency against disease, such as cancer, and therefore have the potential to achieve therapeutic efficacy in the animals described herein.

In an exemplary embodiment, the invention provides a method of treating a disease. The method includes administering to the animal a therapeutically effective amount of the compound of the invention, sufficient to treat the disease. In an exemplary embodiment, the invention provides a method of treating a disease in an animal comprising administering to the animal a therapeutically effective amount of the compound of the invention, wherein the animal is in need of treatment, sufficient to treat the disease. In another aspect, the invention provides a method of treating a disease in an animal comprising administering to the animal a therapeutically effective amount of the compound of the invention, wherein the animal is not otherwise in need of treatment with the compound of the invention, sufficient to treat the disease. In an exemplary embodiment, the disease is fibrosis. In an exemplary embodiment, the disease is fibrosis of the kidney. In an exemplary embodiment, the disease is fibrosis of the liver. In an exemplary embodiment, the disease is fibrosis of the lung. In an exemplary embodiment, the disease is fibrosis of the skin.

In an exemplary embodiment, the disease is a tumor. In an exemplary embodiment, the disease is a tumor, and the tumor is benign, or non-cancerous. In an exemplary embodiment, the disease is a tumor, and the tumor is malignant, or cancerous. In an exemplary embodiment, the disease is a tumor, and the tumor is benign (non-cancerous). In an exemplary embodiment, the disease is cancer. In an exemplary embodiment, the disease is cancer. In an exemplary embodiment, the term "cancer" defines any malignant cancerous growth. In an exemplary embodiment, the disease is a cancer of the blood. In an exemplary embodiment, the disease is leukemia. In an exemplary embodiment, the disease is acute myeloid leukemia. In an exemplary embodiment, the disease is myeloma. In an exemplary embodiment, the disease is cancer of the head. In an exemplary embodiment, the disease is cancer of the neck. In an exemplary embodiment, the disease is cancer of the cervix. In an exemplary embodiment, the disease is non-small cell lung cancer. In an exemplary embodiment, the disease is mesothelioma. In an exemplary embodiment, the disease is cancer of the lung. In an exemplary embodiment, the disease is cancer of the colon. In an exemplary embodiment, the disease is cancer of the breast.

In an exemplary embodiment, the disease is a neurodegenerative disease. In an exemplary embodiment, the disease is amyotrophic lateral sclerosis (ALS). In an exemplary embodiment, the disease is Alzheimer's disease.

In an exemplary embodiment, a compound of the invention treats a disease in an animal, by inhibiting CDK8 and/or CDK19 and/or HIPK2 and/or CK2a activity. The present invention thus provides a method for treating a disease by inhibiting CDK8 and/or CDK19 and/or HIPK2 and/or CK2a activity comprising the step of administering compounds of the invention to an animal in need thereof.

In an exemplary embodiment, a compound of the invention is used at an early stage of a disease, or before early onset, or after significant progression, including metastasis in case of cancer. The term "treatment" or "treating" applied to tumor can refer to a reduction of the burden in an animal, such as a reduction in cell proliferation rate, a destruction of diseased proliferative cells, a reduction of tumor mass or tumor size, a delaying of tumor progression, or a complete tumor suppression.

In an exemplary embodiment, a compound of the invention can be used in any disease state for which CDK8 and/or CDK19 and/or HIPK2 and/or CK2a play a role.

In an exemplary embodiment, the disease is a viral infection. In an exemplary embodiment, the disease is a human papilloma virus. In an exemplary embodiment, the disease is associated with a human papilloma virus infection.

In an exemplary embodiment, the invention provides a use of a compound of a invention in the manufacture of a medicament for the treatment of a disease described herein.

In an exemplary embodiment, a compound of the invention may be administered in a single dose or a series of doses.

In another exemplary embodiment, the animal is a eukaryote. In another exemplary embodiment, the animal is a vertebrate animal. In another exemplary embodiment, the animal is a mammal. In another exemplary embodiment, the animal is a rodent. In another exemplary embodiment, the animal is a mouse. In another exemplary embodiment, the animal is a horse. In another exemplary embodiment, the animal is a primate or a simian. In another exemplary embodiment, the animal is a monkey or an ape. In another exemplary embodiment, the animal is a human or a farm animal or a companion animal. In another exemplary embodiment, the animal is a human. In another exemplary embodiment, the animal is a goat or pig or sheep or horse or cow or bull. In another exemplary embodiment, the animal is a cat. In another exemplary embodiment, the animal is a dog. In another exemplary embodiment, the animal is a rabbit.

VI. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another exemplary embodiment, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form. In another aspect, the invention is a pharmaceutical formulation which includes a combination described herein.

The pharmaceutical formulations of the invention can take a variety of forms adapted to the chosen route of administration. In an exemplary embodiment, the pharmaceutical formulation of the invention is administered orally. In an exemplary embodiment, the pharmaceutical formulation of the invention is in an oral dosage form. Those skilled in the art will recognize various synthetic methodologies that may be employed to prepare non-toxic pharmaceutical formulations incorporating the compounds described herein. Those skilled in the art can utilize a reference such as *Handbook of Pharmaceutical Excipients*, 4th Edition, Edited by Raymond Rowe for information on useful pharmaceutical excipients.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

All temperatures are given in degrees Centigrade. Room temperature means 20 to 25° C. Reagents were purchased from commercial sources or prepared following standard literature procedures. Unless otherwise noted, reactions were carried out under a positive pressure of nitrogen. Reaction vessels were sealed with either rubber septa or Teflon screw caps. Nitrogen was introduced through Tygon tubing, fitted with a large bore syringe needle. Concentration under vacuum refers to the removal of solvent on a Büchi Rotary Evaporator.

Analytical HPLC was performed using a Supelco discovery $C_{18}$ 15 cm×4.6 mm/5 μm column coupled with an Agilent 1050 series VWD UV detector at 210 nm. Conditions: Solvent A: $H_2O$/1% acetonitrile/0.1% $HCO_2H$; Solvent B: methanol.

Proton magnetic resonance ($^1H$ NMR) spectra were recorded on a Varian INOVA NMR spectrometer [400 MHz ($^1H$) or 500 MHz ($^1H$)]. All spectra were determined in the solvents indicated. Although chemical shifts are reported in ppm downfield of tetramethylsilane, they are referenced to the residual proton peak of the respective solvent peak for $^1H$ NMR. Interproton coupling constants are reported in Hertz (Hz).

LCMS spectra were obtained using a ThermoFinnigan AQA MS ESI instrument utilizing a Phenomenex Aqua 5 micron $C_{18}$ 125 Å 50×4.60 mm column. The spray setting for the MS probe was at 350 μL/min with a cone voltage at 25 mV and a probe temperature at 450° C. The spectra were recorded using ELS and UV (254 nm) detection. Alternatively, LCMS spectra were obtained using an Agilent 1200SL HPLC equipped with a 6130 mass spectrometer operating with electrospray ionization.

Silica gel chromatography was carried out on either a Teledyne ISCO CombiFlash Companion or Companion Rf Flash Chromatography System with a variable flow rate from 5-100 mL/min. The columns used were Teledyne ISCO RediSep Disposable Flash Columns (4, 12, 40, 80, or 120 g prepacked silica gel), which were run with a maximum capacity of 1 g crude sample per 10 g silica gel. Samples were preloaded on Celite in Analogix Sample Loading Cartridges with frits (1/in, 1/out). The eluent was 0-100% EtOAc in heptane or 0-10% MeOH in $CH_2Cl_2$ as a linear gradient over the length of the run (14-20 minutes). Peaks were detected by variable wavelength UV absorption (200-360 nm). The resulting fractions were analyzed, combined as appropriate, and evaporated under reduced pressure to provide purified material.

HPLC purification was performed using a 50 mm Varian Dynamax HPLC 21.4 mm Microsorb Guard-8 $C_{18}$ column, Dyonex Chromeleon operating system coupled with a Varian Prostar 320 UV-vis detector (254 nm) and a Sedex55 ELS detector. Conditions: Solvent A: $H_2O$/1% acetonitrile/0.1% $HCO_2H$; Solvent B: MeOH. The appropriate solvent gradient for purification was determined based on the results of analytical HPLC experiments. The resulting fractions were analyzed, combined as appropriate, and evaporated under reduced pressure to provide purified material.

The following experimental sections illustrate procedures for the preparation of intermediates and methods for the preparation of products according to this invention. It should be evident to those skilled in the art that appropriate substitution of both the materials and methods disclosed herein will produce the examples illustrated below and those encompassed by the scope of the invention.

All solvents used were commercially available and were used without further purification. Reactions were typically run using anhydrous solvents under an inert atmosphere of $N_2$.

Compounds are named using the AutoNom 2000 add-on for MDL ISIS™ Draw 2.5 SP2 or their catalogue name if commercially available.

Starting materials used were either available from commercial sources or prepared according to literature procedures and had experimental data in accordance with those reported.

Example 1

Synthesis of Compounds of the Invention

Experimental

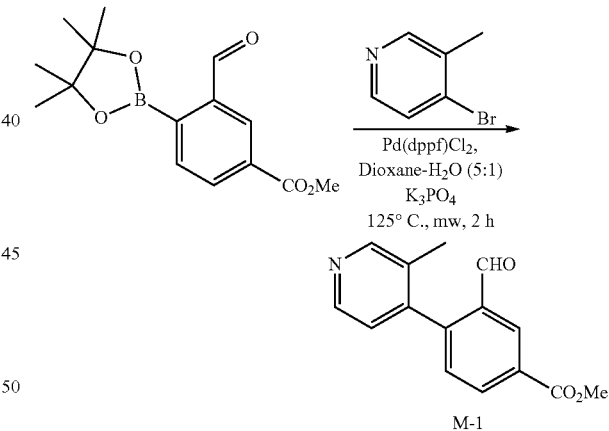

Methyl 3-formyl-4-(3-methylpyridin-4-yl)benzoate (M-1). To a 25 mL vessel were introduced 4-bromo-3-methylpyridine (233.1 mg, 1.317 mmol), methyl 3-formyl-4-(4,4,5,5-tetramethyl-1,3,2-dioxaborolan-2-yl)benzoate (573 mg, 1.975 mmol), $K_3PO_4$ (699 mg, 3.292 mmol) and Pd(dppf)$Cl_2$ (97 mg, 0.131 mmol) in dioxane-water (5 mL-1 mL) and the vessel was placed into the microwave cavity. The microwave source was then turned on and the reaction mixture was irradiated under constant microwave for 2 h at 125° C. After cooling to room temperature, the reaction was concentrated and purified by column chromatography using a mixture of hexane and ethyl acetate to give methyl 3-formyl-4-(3-methylpyridin-4-yl)benzoate (332 mg, 92%). LCMS (ES) for $C_{15}H_{13}NO_3$: m/z 256.1 [M+H]$^+$.

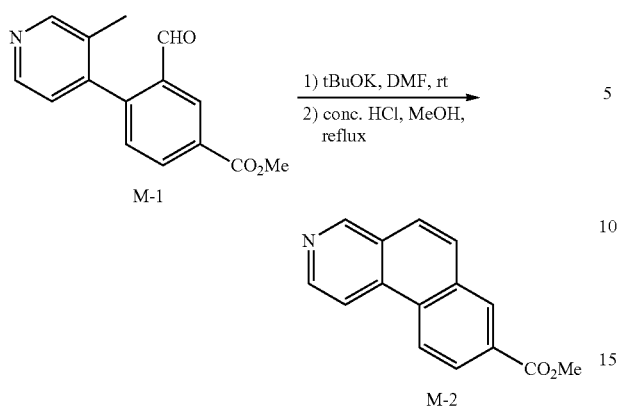

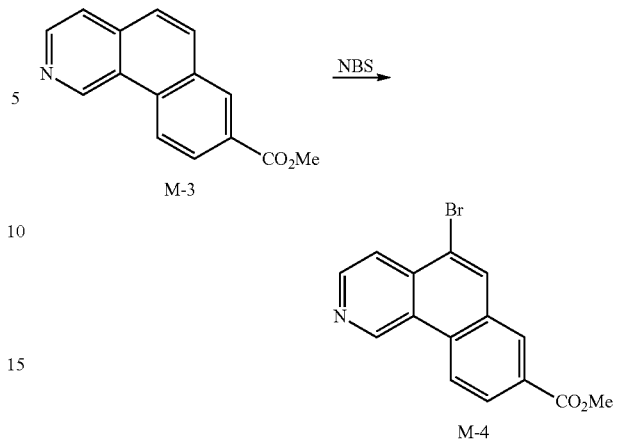

Methyl benzo[f]isoquinoline-8-carboxylate (M-2). To a solution of methyl 3-formyl-4-(3-methylpyridin-4-yl)benzoate (332 mg, 1.303 mmol) in anhydrous DMF (2 mL) was slowly added KOtBu (293 mg, 2.605 mmol) in DMF (2 mL) under $N_2$ environment. The brown suspension was stirred at room temperature overnight and quenched with 1N HCl at 0° C. upon completion of starting material. The resulting mixture was evaporated and further dried in vacuo for 3 h. The solid was dissolved in MeOH (30 mL) and conc. HCl (1 mL) and refluxed for 18 h. After cooling to room temperature, the mixture was quenched with sat. $NaHCO_3$ and extracted with EtOAc (20 mL×3) and the combined organic layers were dried over $MgSO_4$, and concentrated. The crude products were purified by flash column chromatography on silica gel to yield methyl benzo[f]isoquinoline-8-carboxylatetate (54 mg, 18% for two steps). LCMS (ES) for C15H11NO2: m/z 238.3 $[M+H]^+$.

Methyl 5-bromobenzo[h]isoquinoline-8-carboxylate (M-4). To a cooled solution of methyl benzo[f]isoquinoline-8-carboxylatetate (200 mg, 0.84 mmol) in sulfuric acid (4 ml) under ice/water bath was added N-Bromosuccinimide (NBS) (188 mg, 1.05 mmol) with vigorous stirring. The reaction was placed in refrigerator (2° C.) overnight without stirring. The reaction was diluted with ice/water and neutralized with 35% ammonium hydroxide (15 ml), extracted with ethyl acetate. The organic layer was washed with brine, dried over magnesium sulfate, and concentrated to yield 240 mg (92%) of methyl 5-bromobenzo[h]isoquinoline-8-carboxylate, LCMS (ES) for $C_{15}H_{10}BrNO_2$: m/z 316 $[M+H]^+$.

Synthesis of Compounds 1-3

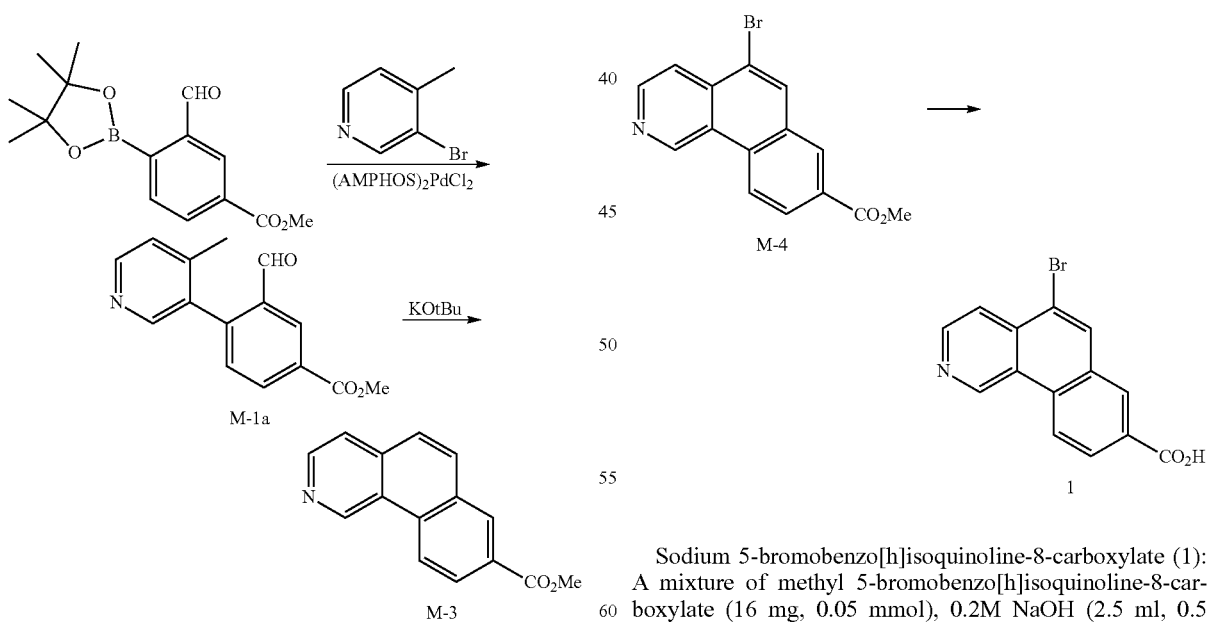

Methyl benzo[h]isoquinoline-8-carboxylate (M-3). Following the procedures similar to M-2 synthesis, the tittle compound was prepared from 3-bromo-4-methylpyridine and methyl 3-formyl-4-(4,4,5,5-tetramethyl-1,3,2-dioxaborolan-2-yl)benzoate.

Sodium 5-bromobenzo[h]isoquinoline-8-carboxylate (1): A mixture of methyl 5-bromobenzo[h]isoquinoline-8-carboxylate (16 mg, 0.05 mmol), 0.2M NaOH (2.5 ml, 0.5 mmol), THF (3 ml), and methanol (2 ml) was stirred overnight at rt. The mixture was acidified with acetic acid and concentrated, dilute with water and filtered to yield 8.1 mg of acid. The acid was converted to sodium salt by adding 1 equivalent 0.2M NaOH and the solution was lyophilized to yield 8.3 mg of sodium 5-bromobenzo[h]isoquinoline-8-carboxylate. 1H NMR (400 MHz, DMSO-d6): δ 10.13 (s, 1H), 8.9 (d, 1H), 8.77 (d, 1H), 8.58 (s, 1H), 8.44 (s, 1H), 8.22 (d, 1H), 8.00 (d, 1H) ppm. LCMS (ES) for C14H8BrNO2: m/z 302 [M+H].

Sodium benzo[h]isoquinoline-8-carboxylate (2). This compound was prepared from M-3 in a similar method as Example 1. $^1$H NMR (400 MHz, DMSO-d6): δ 10.1 (s, 1H), 8.92 (d, 1H), 8.67 (d, 1H), 8.51 (s, 1H), 8.25 (dd, 1H), 8.14 (dd, 1H), 7.88 (d, 1H), 7.82 (dd, 1H) ppm. LCMS (ES) for C14H9NO2: m/z 224 [M+H].

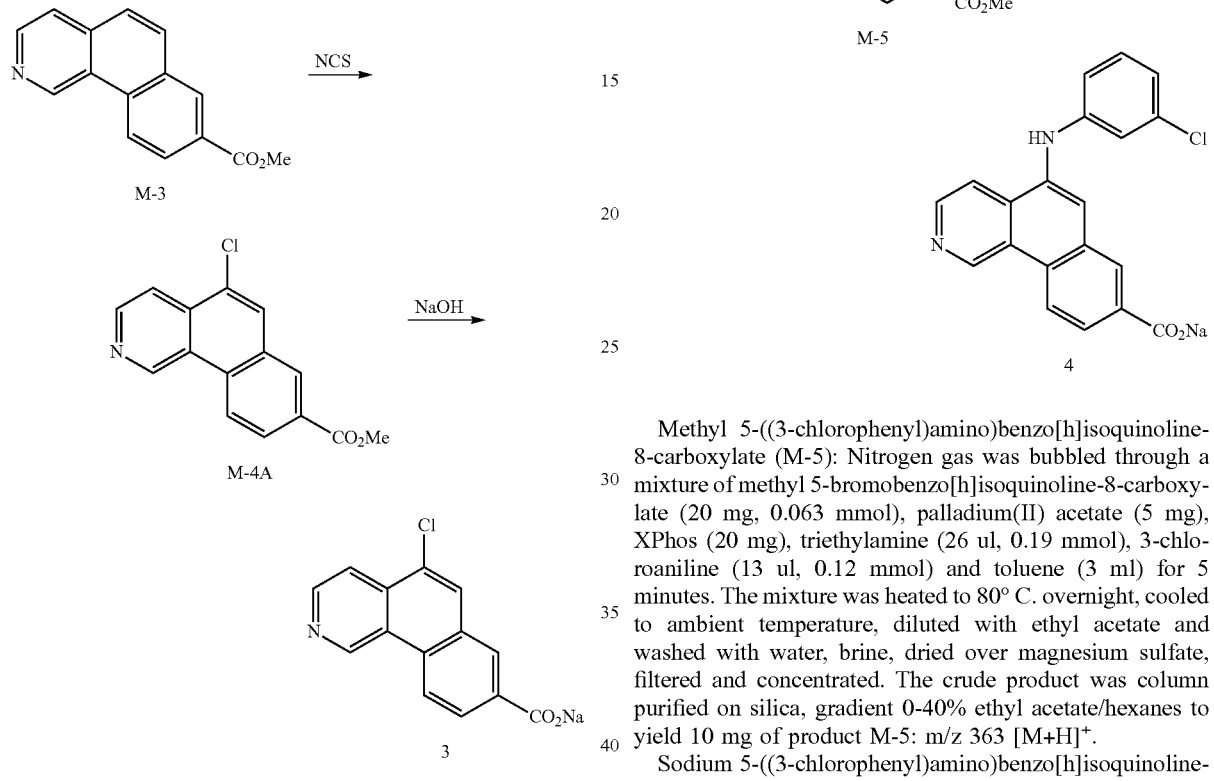

Sodium 5-chlorobenzo[h]isoquinoline-8-carboxylate (3): The conversion of M-3 to methyl 5-chlorobenzo[h]isoquinoline-8-carboxylate (M-4A) is similar to the synthesis of M-4 by using N-chlorosuccinimide (NCS). M-4A was then converted to the title compound in a similar fashion as Example 1: $^1$H NMR (400 MHz, DMSO-d6): δ 10.21 (s, 1H), 8.93 (d, 1H), 8.82 (d, 1H), 8.48 (s, 1H), 8.43 (s, 1H), 8.25 (dd, 1H), 7.12 (d, 1H) ppm. LCMS (ES) for C14H8ClNO2: m/z 258 [M+H]$^+$.

Synthesis of Compounds 4-5

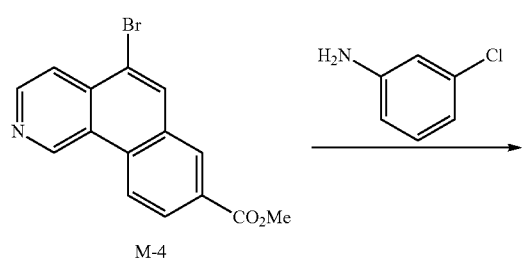

Methyl 5-((3-chlorophenyl)amino)benzo[h]isoquinoline-8-carboxylate (M-5): Nitrogen gas was bubbled through a mixture of methyl 5-bromobenzo[h]isoquinoline-8-carboxylate (20 mg, 0.063 mmol), palladium(II) acetate (5 mg), XPhos (20 mg), triethylamine (26 ul, 0.19 mmol), 3-chloroaniline (13 ul, 0.12 mmol) and toluene (3 ml) for 5 minutes. The mixture was heated to 80° C. overnight, cooled to ambient temperature, diluted with ethyl acetate and washed with water, brine, dried over magnesium sulfate, filtered and concentrated. The crude product was column purified on silica, gradient 0-40% ethyl acetate/hexanes to yield 10 mg of product M-5: m/z 363 [M+H]$^+$.

Sodium 5-((3-chlorophenyl)amino)benzo[h]isoquinoline-8-carboxylate (4): This compound was prepared from M-5 in a similar method as Example 1. $^1$H NMR (400 MHz, DMSO-d6): δ 10.17 (s, 1H), 8.82 (d, 1H), 8.71 (d, 1H), 8.53 (s, 1H), 8.31 (s, 1H), 8.12 (d, 1H), 7.99 (d, 1H), 7.89 (s, 1H), 7.23 (t, 1H), 6.99 (m, 2H), 6.83 (dd, 1H) ppm. LCMS (ES) for C20H13ClN2O2: m/z 349 [M+H].

Sodium 5-((4-chlorophenyl)amino)benzo[h]isoquinoline-8-carboxylate (5): This compound was prepared from M-4 and 4-chloroaniline in the similar method of Example 2 described above. LCMS (ES) for C20H13ClN2O2: m/z 349 [M+H].

Synthesis of Compounds 6-8

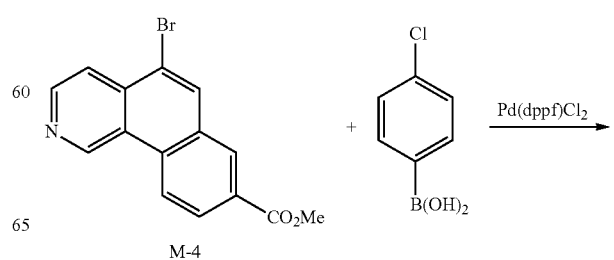

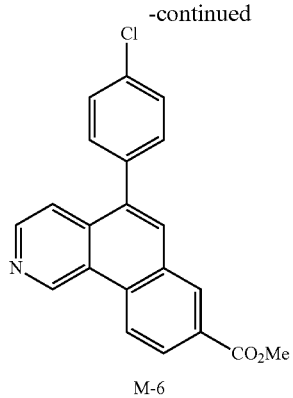

M-6

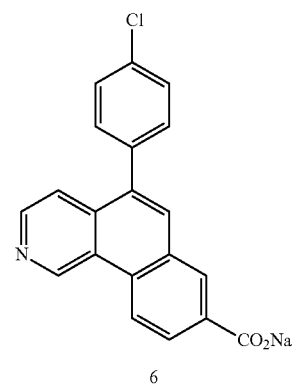

6

Methyl 5-(4-chlorophenyl)benzo[h]isoquinoline-8-carboxylate (M-6): Nitrogen gas was bubbled through a mixture of methyl 5-bromobenzo[h]isoquinoline-8-carboxylate (20 mg, 0.063 mmol), Pd(dppf)Cl$_2$ (5 mg), cesium fluoride (48 mg, 0.32 mmol), 4-chlorophenylboronic acid (15 mg, 0.95 mmol) and dioxane (3 ml) for 5 minutes. The mixture was heated to 80° C. for 24 hours, cooled to ambient temperature, diluted with ethyl acetate and washed with water, brine, dried over magnesium sulfate, filtered and concentrated. The crude product was column purified on silica, 0-40% ethyl acetate/hexanes to yield 17 mg of methyl 5-(4-chlorophenyl)benzo[h]isoquinoline-8-carboxylate (M-6): m/z 348 [M+H]$^+$.

Sodium 5-(4-chlorophenyl)benzo[h]isoquinoline-8-carboxylate (6): A mixture of methyl 5-(4-chlorophenyl)benzo[h]isoquinoline-8-carboxylate (17 mg), lithium hydroxide hydrate (25 mg), THF (3 ml), MeOH (1 ml), and water (1 ml) was stirred at rt overnight. The reaction was concentrated, diluted with water, neutralized with acetic acid and filtered to gave 8.2 mg acid. The acid was converted to sodium salt by adding 1 equivalent of 0.2M NaOH and lyophilized to yield 7.4 mg product the tittle compound: 1H NMR (400 MHz, DMSO-d6): δ 10.27 (s, 1H), 9.09 (d, 1H), 8.70 (d, 1H), 8.66 (s, 1H), 8.26 (d, 1H), 8.19 (s, 1H), 7.64 (m, 5H) ppm. LCMS (ES) for C20H12ClNO2: m/z 334 [M+H]$^+$.

The following compounds were prepared in the similar method described above:

Sodium 5-(pyridin-3-yl)benzo[h]isoquinoline-8-carboxylate (7): 1H NMR (400 MHz, DMSO-d6): δ 10.24 (s, 1H), 8.94 (d, 1H), 8.77 (s, 1H), 8.71 (d, 1H), 8.66 (d, 1H), 8.53 (s, 1H), 8.28 (d, 1H), 8.15 (s, 1H), 8.03 (dd, 1H), 7.60 (m, 2H) ppm. LCMS (ES) for C$_{19}$H$_{12}$N$_2$O$_2$: m/z 301 [M+H]$^+$.

Sodium 5-(pyridin-4-yl)benzo[h]isoquinoline-8-carboxylate (8): 1H NMR (400 MHz, DMSO-d6): δ 10.25 (s, 1H), 8.98 (d, 1H), 8.76 (m, 2H), 8.67 (d, 1H), 8.56 (s, 1H), 8.28 (d, 1H), 8.18 (s, 1H), 7.66 (d, 1H), 7.62 (m, 2H) ppm. LCMS (ES) for C19H12N2O2: m/z 301 [M+H]$^+$.

Synthesis of Compounds 9-11

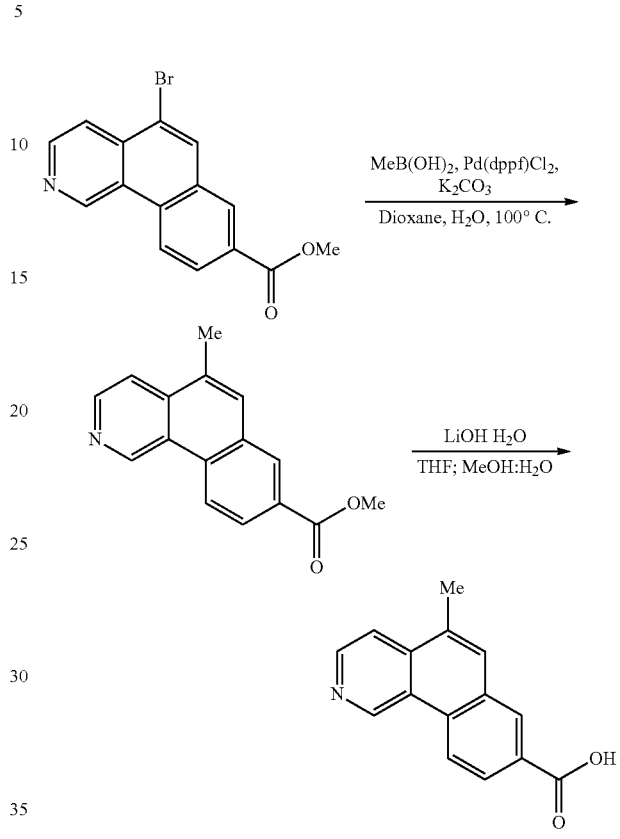

9

Sodium 5-methylbenzo[h]isoquinoline-8-carboxylate (9): A mixture of methyl 5-bromobenzo[h]isoquinoline-8-carboxylate (28.7 mg, 0.090 mmol), methylboronic acid (200 mg, 3.341 mmol), Pd(dppf)Cl$_2$ (0.7 mg, 0.009 mmol) and potassium carbonate (38 mg, 0.270 mmol) in dioxane-water (3 mL-1 mL) was heated at 100° C. for 18 hours. The mixture was diluted with EtOAc (10 mL) and water (10 mL). The aqueous layer was extracted with EtOAc (20 mL×3). The combined organic layers were washed with brine, water and dried over MgSO$_4$. The mixture was filtered and concentration under reduced pressure. The crude product was then purified by column chromatography (EtOAc/Hexane) to give a methyl 5-methylbenzo[h]isoquinoline-8-carboxylate. LCMS (ES) for C16H13NO2: m/z 252.2 [M+H]$^+$.

To a solution of methyl 5-methylbenzo[h]isoquinoline-8-carboxylate (4 mg, 0.01 mmol,) in THF/MeOH/H$_2$O (2 mL, 2:1:1) was added LiOH (5 mg, 0.11 mmol) and stirred for 10 h at room temperature. The resulting mixture was evaporated to ca. 1 mL of mixture and added 0.5 mL of AcOH. The suspension was filtered, concentrated and purified by preparative HPLC to give a 5-methylbenzo[h]isoquinoline-8-carboxylic acid. The corresponding acid was treated with 1 eq. of NaOH in water/acetonitrile, followed by lyophilization to give a sodium salt of 5-methylbenzo[h]isoquinoline-8-carboxylic acid. 1H NMR (400 MHz, DMSO-d6): δ 10.1 (s, 1H), 8.86 (d, 1H), 8.73 (d, 1H), 8.38 (s, 1H), 8.18 (dd, 1H), 7.96 (s, 1H), 7.93 (dd, 1H) ppm. LCMS (ES) for C15H11NO2: m/z 238 [M+H]$^+$.

The following compounds were prepared in analogous methods as described in Example 4 above:

Sodium 5-(6-aminopyridin-3-yl)benzo[h]isoquinoline-8-carboxylate (10): 1H NMR (400 MHz, DMSO-d6): δ 10.2 (s, 1H), 8.90 (d, 1H), 8.65 (d, 1H), 8.47 (s, 1H), 8.23 (dd, 1H), 8.10 (d, 1H), 8.00 (s, 1H), 7.73 (d, 1H), 7.59 (dd, 1H), 6.63 (d, 1H), 6.18 (d, 1H) ppm. LCMS (ES) for C19H13N3O2: m/z 316 [M+H]+.

Sodium 5-(1H-pyrazol-3-yl)benzo[h]isoquinoline-8-carboxylate (11): $^1$H NMR (400 MHz, DMSO-d6): δ 10.2 (s, 1H), 8.90 (d, 1H), 8.70 (d, 1H), 8.50 (s, 1H), 8.31 (s, 1H), 8.24 (d, 1H), 7.90 (s, 1H), 7.64 (bs, 1H), 6.81 (d, 1H), 6.54 (d, 1H) ppm. LCMS (ES) for $C_{17}H_{11}N_3O_2$: m/z 290 [M+H]+.

Synthesis of Compounds 12-22

Sodium 5-(cyclohexylamino)benzo[h]isoquinoline-8-carboxylate (12)

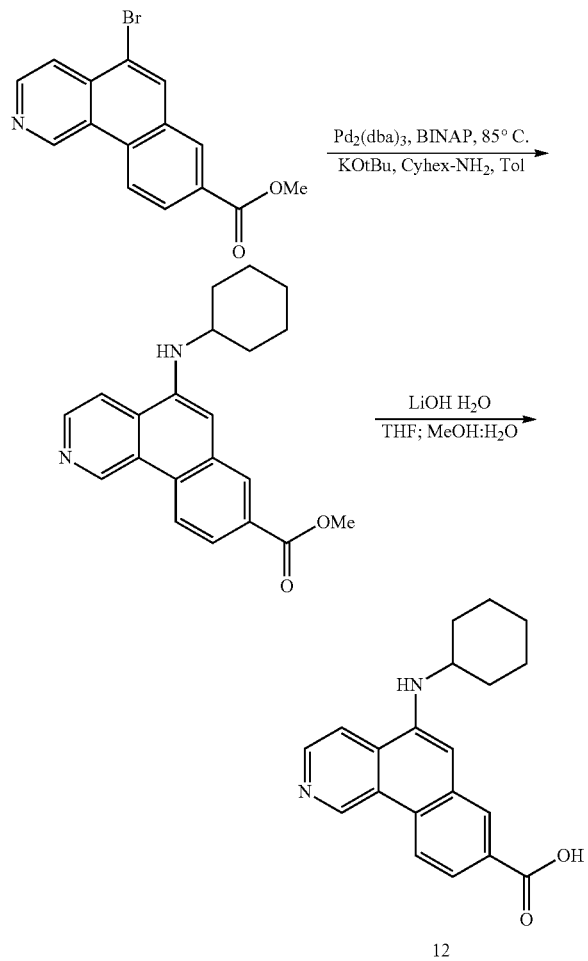

To a solution of methyl 5-bromobenzo[h]isoquinoline-8-carboxylate (28.7 mg, 0.090 mmol), KOtBu (19 mg, 0.169 mmol), BINAP (8 mg, 0.012 mmol) and Pd2(dba)3 (6 mg, 0.006 mmol) in toluene (4 mL) was added a cyclohexylamine (12 mg, 0.121 mmol) and the mixture was heated to 85° C. for 4 h. The resulting mixture was concentrated in vacuo. The crude mixture was purified by column chromatography to give an methyl 5-(cyclohexylamino)benzo[h] isoquinoline-8-carboxylate. LCMS (ES) for C21H22N2O2 m/z 335.4 [M+H]+.

The methyl ester was dissolved in a 2:1:1 mixture of THF, methanol, and water (2 mL). LiOH (20 mg) was added and the resulting mixture stirred at room temperature for 18 h. Water, methanol, and acetic acid were added and the solution purified by preparative HPLC to give a title compound, 5-(cyclohexylamino)benzo[h]isoquinoline-8-carboxylic acid. The corresponding acid was treated with 1 eq. of NaOH in water/acetonitrile, followed by lyophilization to give a sodium 5-(cyclohexylamino)benzo[h]isoquinoline-8-carboxylate. $^1$H NMR (400 MHz, DMSO-d6): δ 10.0 (s, 1H), 8.64 (d, 1H), 8.60 (dd, 1H), 8.19 (m, 2H), 7.85 (dd, 1H), 8.96 (s, 1H), 5.82 (d, 1H), 3.53 (m, 1H), 2.13 (dd, 2H), 1.80 (m, 2H), 1.68 (m, 1H), 1.35 (m, 4H), 1.23 (m, 1H) ppm. LCMS (ES) for C20H20N2O2: m/z 321 [M+H]+, >98% pure.

The following compounds were prepared in the analogous method to Example 5 described above:

(R)-5-(Piperidin-3-ylamino)benzo[h]isoquinoline-8-carboxylic acid (13): 1H NMR (400 MHz, DMSO-d6): δ 10.2 (s, 1H), 9.05 (d, 1H), 8.82 (d, 1H), 8.64 (s, 1H), 8.12 (d, 1H), 8.01 (bs, 1H), 7.84 (s, 1H), 3.82-8.50 (m, 4H), 2.65 (m, 1H), 2.05 (m, 2H), 1.85 (m, 2H) ppm. LCMS (ES) for C19H19N3O2: m/z 322 [M+H]+.

(R)-5-(3-Aminopiperidin-1-yl)benzo[h]isoquinoline-8-carboxylic acid (14): 1H NMR (400 MHz, DMSO-d6): δ 10. 3 (s, 1H), 9.20 (bs, 1H), 9.18 (bs, 1H), 8.96 (d, 1H), 8.89 (d, 1H), 8.63 (bs, 1H), 8.49 (s, 1H), 7.96 (d, 1H), 7.46 (s, 1H), 6.64 (m, 1H), 4.05 (m, 1H), 3.69 (m, 1H), 2.95 (m, 1H), 2.70 (dd, 1H), 2.32 (m, 1H), 2.15 (m, 1H), 1.98 (m, 1H), 1.80 (m, 1H) ppm. LCMS (ES) for C19H19N3O2: m/z 322 [M+H]+.

Sodium 5-(cyclopentylamino)benzo[h]isoquinoline-8-carboxylate (15): 1H NMR (400 MHz, DMSO-d6): δ 10.0 (s, 1H), 8.63 (d, 1H), 8.60 (dd, 1H), 8.18 (d, 1H), 8. 17 (d, 1H), 7.85 (dd, 1H), 6.91 (s, 1H), 5.94 (d, 1H), 4.00 (m, 1H), 2.11 (m, 2H), 1.78-1.60 (m, 6H) ppm. LCMS (ES) for C19H18N2O2: m/z 307 [M+H]+.

Sodium 5-(sec-butylamino)benzo[h]isoquinoline-8-carboxylate (16): 1H NMR (400 MHz, DMSO-d6): δ 10.0 (s, 1H), 8.66 (d, 1H), 8.61 (dd, 1H), 8.20 (d, 1H), 8.18 (s, 1H), 7.85 (dd, 1H), 6.88 (s, 1H), 6.25 (t, 1H), 3.11 (m, 2H), 2.13 (m, 1H), 1.02 (d, 6H) ppm. LCMS (ES) for C18H18N2O2: m/z 295 [M+H]+.

Sodium 5-(cyclopropylamino)benzo[h]isoquinoline-8-carboxylate (17): 1H NMR (400 MHz, DMSO-d6): δ 10.0 (s, 1H), 8.64 (d, 1H), 8.62 (d, 1H), 8.20 (s, 1H), 8.02 (d, 1H), 7.88 (dd, 1H), 7.27 (s, 1H), 6.70 (s, 1H), 2.60 (m, 1H), 0.87 (m, 2H), 0.58 (m, 2H) ppm. LCMS (ES) for C17H14N2O2: m/z 279 [M+H]+.

Sodium 5-(cyclobutylamino)benzo[h]isoquinoline-8-carboxylate (18): 1H NMR (400 MHz, DMSO-d6): δ 10.0 (s, 1H), 8.65 (d, 1H), 8.62 (dd, 1H), 8.18 (s, 1H), 817 (s, 1H), 7.87 (dd, 1H), 6.79 (s, 1H), 6.35 (d, 1H), 4.18 (m, 1H), 2.53 (m 2H), 2.05 (m, 2H), 1.85 (m, 2H) ppm. LCMS (ES) for C18H16N2O2: m/z 293 [M+H]+.

(S)-5-(sec-Butylamino)benzo[h]isoquinoline-8-carboxylic acid (19): 1H NMR (400 MHz, DMSO-d6): δ 10.0 (s, 1H), 8.65 (d, 1H), 8.60 (dd, 1H), 8.16 (s, 1H), 7.85 (dd, 1H), 6.89 (s, 1H), 5.80 (d, 1H), 3.67 (m, 1H), 1.7 (m, 1H), 1.57 (m, 1H), 1.27 (d, 3H), 0.99 (t, 3H) ppm. LCMS (ES) for C18H18N2O2: m/z 295 [M+H]+.

Sodium 5-(piperidin-1-yl)benzo[h]isoquinoline-8-carboxylate (20): 1H NMR (400 MHz, DMSO-d6): δ 10.0 (s, 1H), 8.73 (d, 1H), 8.67 (d, 1H), 8.44 (s, 1H), 8.08 (d, 1H), 7.94 (d, 1H), 7.56 (s, 1H), 3.03 (m, 2H), 1.80 (m, 4H), 1.64 (m, 4H) ppm. LCMS (ES) for C19H18N2O2: m/z 307 [M+H]+.

Sodium 5-(isopropylamino)benzo[h]isoquinoline-8-carboxylate (21): 1H NMR (400 MHz, DMSO-d6): δ 10.0 (s, 1H), 8.53 (d, 1H), 8.60 (d, 1H), 8.16 (m, 2H), 7.85 (dd, 1H), 6.92 (s, 1H), 5.83 (d, 1H), 3.88 (m, 1H), 1.31 (d, 6H) ppm. LCMS (ES) for C17H16N2O2: m/z 281 [M+H]+.

Sodium (R)-5-(sec-butylamino)benzo[h]isoquinoline-8-carboxylate (22): 1H NMR (400 MHz, DMSO-d6): δ 10.2 (s, 1H), 8.84 (d, 1H), 8.75 (m, 1H), 8.37 (s, 1H), 8.29 (d, 1H), 7.83 (dd, 1H), 7.04 (s, 1H), 6.07 (d, 1H), 3.78 (m, 1H), 1.79 (m, 1H), 1.58 (m, 1H), 1.30 (d, 3H), 1.02 (t, 3H) ppm. LCMS (ES) for C18H18N2O2: m/z 295 [M+1-1]+.

Synthesis of Compounds 23-25

Sodium 5-bromo-1-chlorobenzo[h]isoquinoline-8-carboxylate (23) and sodium 5-bromo-3-chlorobenzo[h]isoquinoline-8-carboxylate (24)

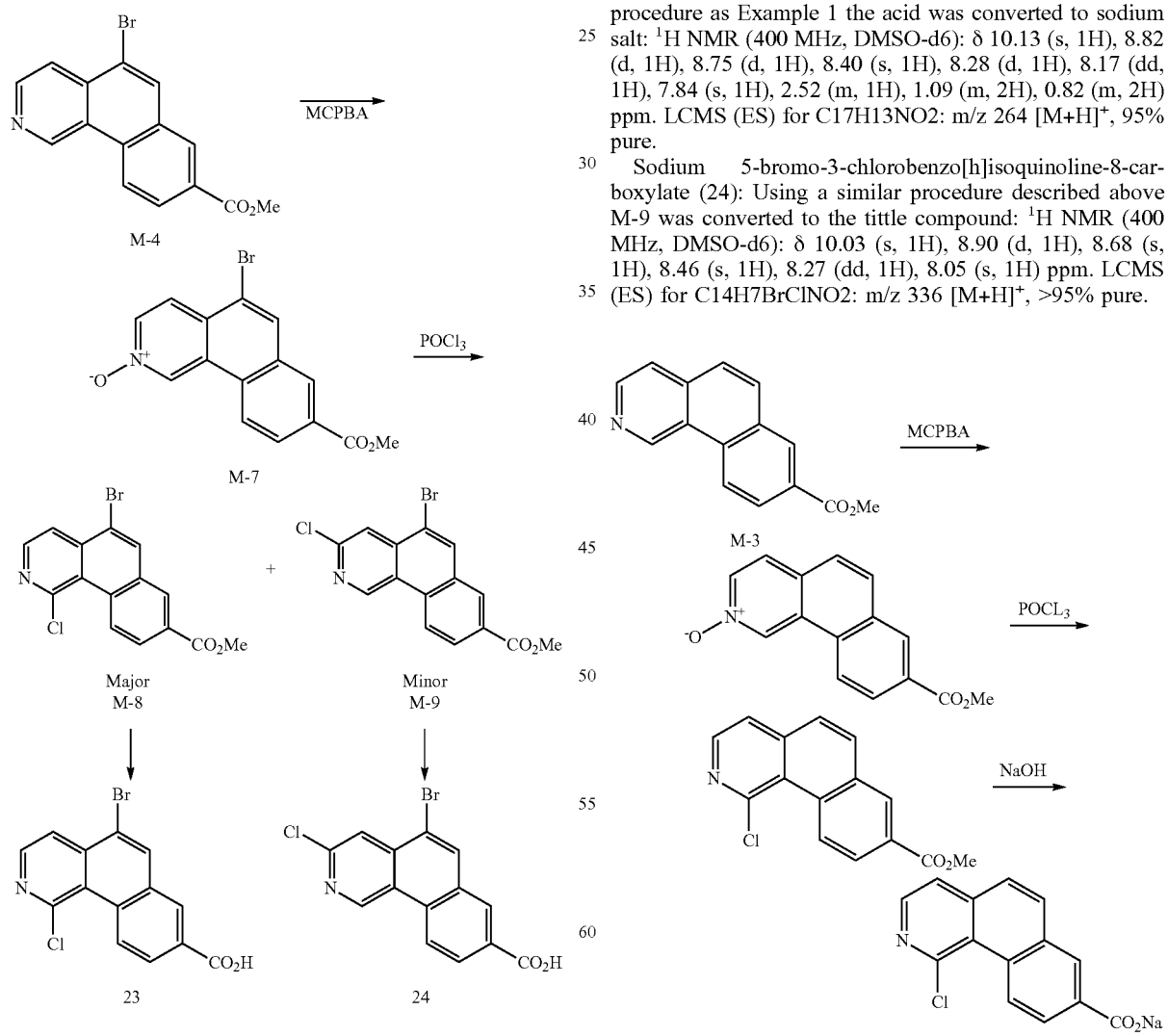

5-bromo-8-(methoxycarbonyl)benzo[h]isoquinoline 2-oxide (M-7): To a solution of methyl 5-bromobenzo[h]isoquinoline-8-carboxylate (0.954 g, 3.0 mmol) in DCM (100 ml) and methanol (20 ml) under ice/water bath was added MCPBA (1.42 g, 6.3 mmol) with stirring. The mixture was stirred at rt overnight. The reaction was washed with sat. NaHCO3 (3 times). The precipitate was collected by filtration to give pure M-7 (0.45 g). The remaining organic filtrate was then passed through a plug of solid K2CO3 to remove any remaining mCPBA. The resulting DCM filtrate was concentrated to yield an additional 0.45 g of M-7. Total yield 0.90 g, m/z 332 [M+H] Total yield 0.90 g, m/z 332 [M+H]+.

Methyl 5-bromo-1-chlorobenzo[h]isoquinoline-8-carboxylate (M-8), and Methyl 5-bromo-3-chlorobenzo[h]isoquinoline-8-carboxylate (M-9): A mixture of 5-bromo-8-(methoxycarbonyl)benzo[h]isoquinoline 2-oxide (60 mg) in POCl3 (2.5 ml) was heated to 115° C. for 1 hour, concentrated, and diluted with DCM followed by water. DCM layer concentrated and column on silica using as DCM as eluent to give M-8 (24 mg) and M-9 (14 mg), m/z 350, 352 [M+H]+. Both products can be distinguished by HNMR.

Sodium 5-bromo-1-chlorobenzo[h]isoquinoline-8-carboxylate (23): A mixture of M-8 (85 mg), LiOH (80 mg), THF (10 ml) and water (3 ml) was stirred for 2 hours, concentrated to remove organic solvent and acidified with acidic acid, and filtered to give 5-bromo-1-chlorobenzo[h]isoquinoline-8-carboxylic acid (75 mg). Using the similar procedure as Example 1 the acid was converted to sodium salt: ¹H NMR (400 MHz, DMSO-d6): δ 10.13 (s, 1H), 8.82 (d, 1H), 8.75 (d, 1H), 8.40 (s, 1H), 8.28 (d, 1H), 8.17 (dd, 1H), 7.84 (s, 1H), 2.52 (m, 1H), 1.09 (m, 2H), 0.82 (m, 2H) ppm. LCMS (ES) for C17H13NO2: m/z 264 [M+H]+, 95% pure.

Sodium 5-bromo-3-chlorobenzo[h]isoquinoline-8-carboxylate (24): Using a similar procedure described above M-9 was converted to the tittle compound: ¹H NMR (400 MHz, DMSO-d6): δ 10.03 (s, 1H), 8.90 (d, 1H), 8.68 (s, 1H), 8.46 (s, 1H), 8.27 (dd, 1H), 8.05 (s, 1H) ppm. LCMS (ES) for C14H7BrClNO2: m/z 336 [M+H]+, >95% pure.

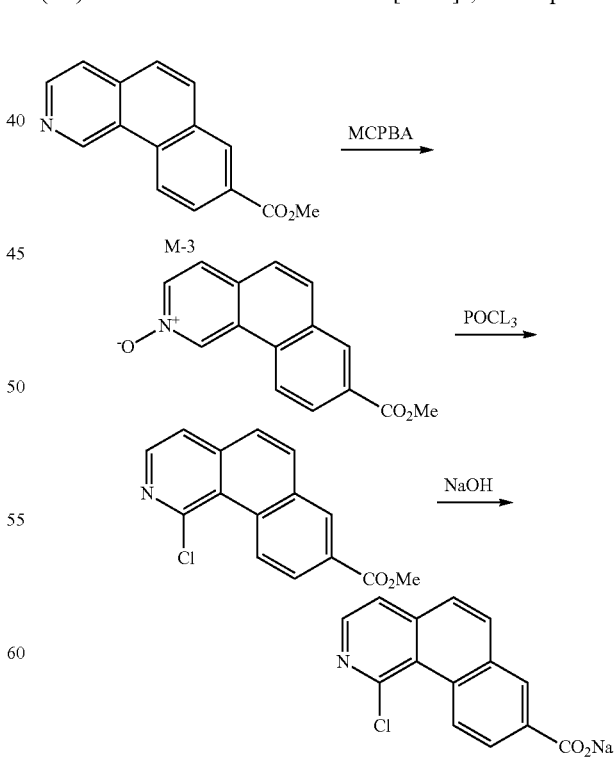

25

Sodium 1-chlorobenzo[h]isoquinoline-8-carboxylate (25). The tittle compound was prepared from M-3 in a similar procedure as Example 6: $^1$H NMR (400 MHz, DMSO-d6): δ 9.64 (d, 1H), 8.49 (s, 1H), 8.45 (d, 1H), 8.23 (dd, 1H), 8.21 (d, 1H), 7.98 (d, 1H), 7.87 (d, 1H) ppm. LCMS (ES) for C14H8ClNO2: m/z 258 [M+H]$^+$, 95% pure.

Synthesis of Compound 26

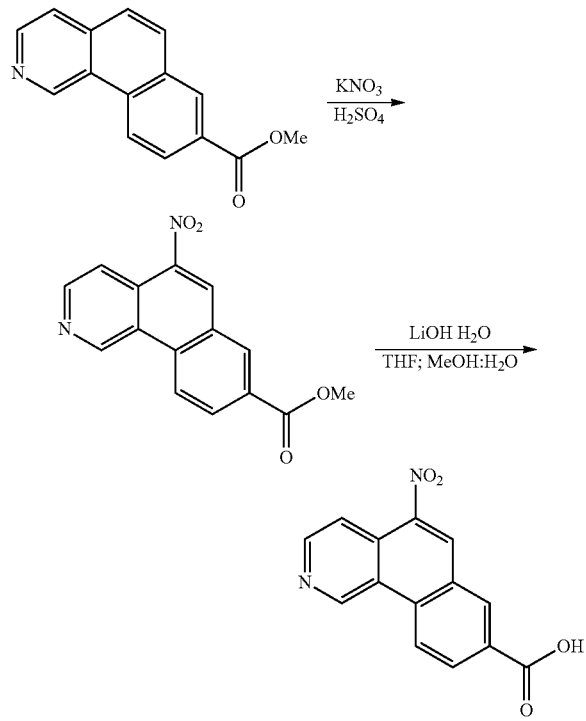

Sodium 5-nitrobenzo[h]isoquinoline-8-carboxylate (26). To a solution of methyl benzo[h]isoquinoline-8-carboxylate (480 mg, 2.025 mmol) in conc. sulfuric acid (4 mL) was added portion wise KNO$_3$ (614 mg, 6.075 mmol) at 0° C. The reaction mixture was stirred for 0.5 h at 0° C. and was poured into an ice-filled flask. The resulting mixture was basified with NH$_4$OH to pH 8-9 and extracted with EtOAc (30 mL×3). The organic phase was dried over MgSO$_4$, and the solvent was removed in vacuo to afford a yellow solid. The solid was triturated with EtOAc to yield a methyl 5-nitrobenzo[h]isoquinoline-8-carboxylate as a pale yellow solid. LCMS (ES) for $C_{15}H_{10}N_2O_4$: m/z 283.1 [M+H]$^+$.

The methyl 5-nitrobenzo[h]isoquinoline-8-carboxylate (41.1 mg, 0.145 mmol) was dissolved in a 2:1:1 mixture of THF, methanol, and water (4 mL). LiOH (18 mg, 0.436 mmol) was added and the resulting mixture stirred at room temperature for 18 h. Water, methanol, and acetic acid were added and the solution purified by preparative HPLC to give a 5-nitrobenzo[h]isoquinoline-8-carboxylic acid. The solid was treated with 0.2N NaOH (1.0 eq) in acetonitrile and lyophilized to give a sodium 5-nitrobenzo[h]isoquinoline-8-carboxylate: $^1$H NMR (400 MHz, DMSO-d6): δ 10.3 (s, 1H), 9.20 (s, 1H), 9.11 (d, 1H), 8.88 (d, 1H), 8.81 (bs, 1H), 8.43 (dd, 1H), 8.33 (d, 1H) ppm. LCMS (ES) for $C_{14}H_8N_2O_4$: m/z 269 [M+H]$^+$.

Synthesis of Compound 27

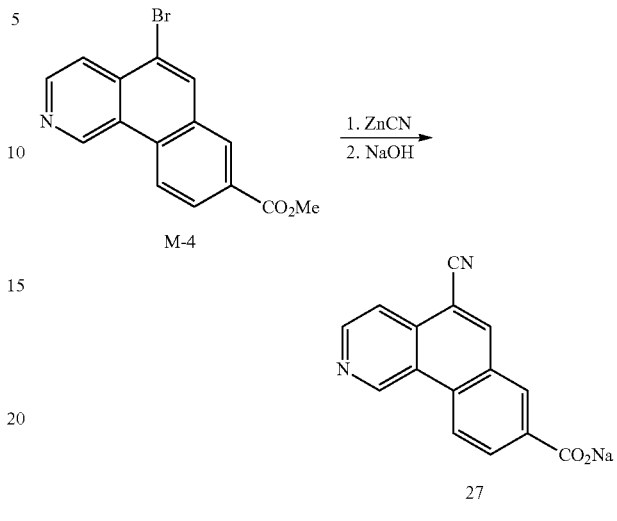
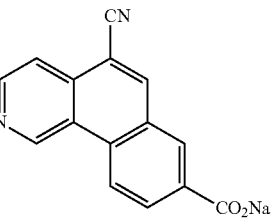

Sodium 5-cyanobenzo[h]isoquinoline-8-carboxylate (27): A mixtures of M-4 (45.2 mg, 0.01 mmol), Zinc cyanide (13 mg, 0.01 mmol), Pd(dppf)Cl$_2$ (14 mg), poly(methylhydrosiloxane) (4 drops), and NMP (2 ml) was heated to 120° C. for 1 hr. After cooling to rt, the reaction mixture was quenched with water, filtered. The filtrate was concentrated in vacuum and separated by column chromatography on silica, eluted with EtOAc:DCM:Hexanes (2:1:1), to give the cyano ester (90% pure). The ester was hydrolyzed and converted to desire sodium salt in a similar fashion as Example 1: $^1$H NMR (400 MHz, DMSO-d6): δ 10.21 (s, 1H), 8.94 (m, 2H), 8.81 (d, 1H), 8.55 (s, 1H), 8.35 (dd, 1H), 7.94 (s, 1H) ppm. LCMS (ES) for C15H8N2O2: m/z 249 [M+H]+.

Synthesis of Compound 28

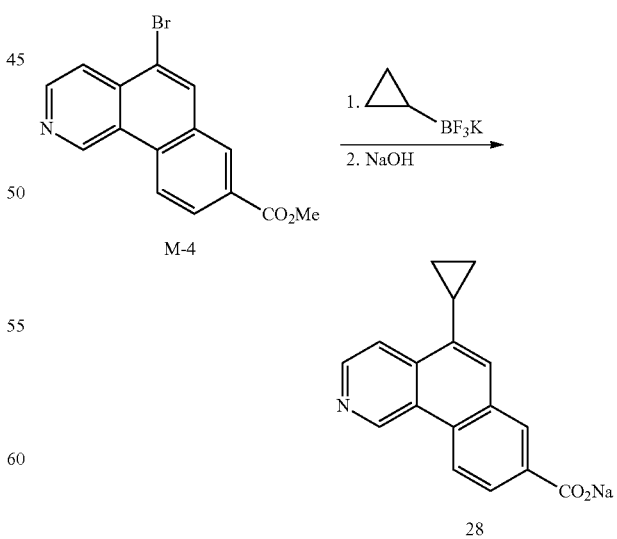
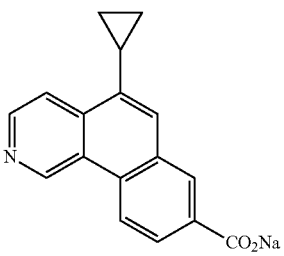

Sodium 5-cyclopropylbenzo[h]isoquinoline-8-carboxylate (28): A mixture of methyl 5-bromobenzo[h]isoquinoline-8-carboxylate (25 mg, 0.08 mmol), potassium cyclopropyltrifluoroborate (35 mg, 0.24 mmol), Pd(dppf)Cl$_2$ (11 mg), Cs$_2$CO$_3$ (130 mg, 0.4 mmol), THF (2 ml), and water (0.2 ml) under nitrogen was heated with at 85° C. overnight. The reaction mixture was diluted with EtOAc, filtered through celite. The filtrated was concentrated in vacuum and purified on flash chromatography (silica, gradient 0-30% EtOAc/hexanes) to give 4 mg the desire ester intermediate. Using the same method as Example 1, the ester was hydrolyzed and converted to the sodium salt (1.5 mg). $^1$H NMR (400 MHz, DMSO-d6): δ 10.13 (s, 1H), 8.82 (d, 1H), 8.75 (d, 1H), 8.40 (s, 1H), 8.28 (d, 1H), 8.17 (dd, 1H), 7.84 (s, 1H), 2.52 (m, 1H), 1.09 (m, 2H), 0.82 (m, 2H) ppm. LCMS (ES) for C17H13NO$_2$: m/z 264 [M+H]$^+$.

Synthesis of Compounds 29-32

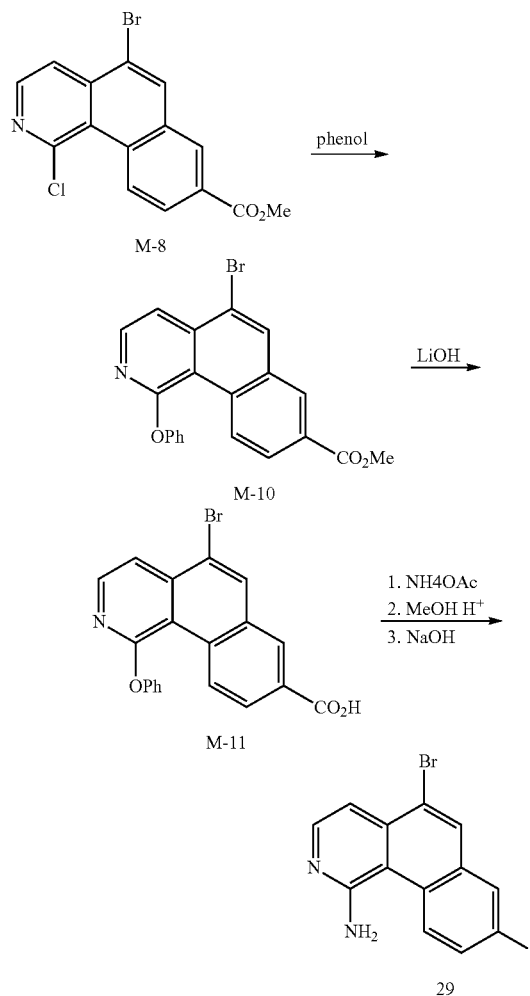

Methyl 5-bromo-1-phenoxybenzo[h]isoquinoline-8-carboxylate (M-10): To a mixture of phenol (76 mg, 0.8 mmol), Cs$_2$CO$_3$ (326 mg, 1 mmol) in DMF (12 ml) was added M-8 (200 mg, 0.57 mmol). The resulting mixture was stirred at rt overnight. The reaction mixture was quenched with water and filtered through celite. The filtrate was purified on flash chromatography (silica, DCM as solvent) to yield M-10 (140 mg): m/z 408 [M+H]$^+$.

5-bromo-1-phenoxybenzo[h]isoquinoline-8-carboxylic acid (M-11): A mixture of M-10 (108 mg), LiOH hydrate (110 mg), THF (20 ml), and water (6 ml) was stirred at rt for 16 hours. Reaction mixture was concentrated, diluted with water and acidified with HOAc, and filtered to yield M-11 (90 mg): m/z 394 [M+H]$^+$.

Sodium 1-amino-5-bromobenzo[h]isoquinoline-8-carboxylate (29): A mixture of M-11 (90 mg) and ammonium acetate (1900 mg) was heated at 145° C. in a sealed tube for 3 days. The reaction mixture was dilute with water and filtered to give crude amino product which was then refluxed for 16 hours in methanol with catalytic sulfuric acid. The resulting crude ester solution was concentrated, treated with NH$_4$OH, filtered. The solid was purified by column chromatography on silica (1:1 EtOAc/hexanes) to yield 54 mg of the ester. The ester was hydrolyzed to the acid and converted to desire sodium 1-amino-5-bromobenzo[h]isoquinoline-8-carboxylate (30 mg): $^1$H NMR (400 MHz, DMSO-d6): δ 8.98 (d, 1H), 8.45 (s, 1H), 8.38 (s, 1H), 8.16 (dd, 1H), 8.12 (d, 1H), 7.33 (d, 1H), 6.66 (br s, 2H) ppm. LCMS (ES) for C$_{14}$H$_9$BrN$_2$O$_2$: m/z 317 [M+H]$^+$.

The following compounds were prepared in the analogous method to Example 10 described above.

Sodium 5-bromo-1-(dimethylamino)benzo[h]isoquinoline-8-carboxylate (30)$^1$H NMR (400 MHz, DMSO-d6): δ 9.00 (d, 1H), 8.50 (s, 1H), 8.37 (s, 1H), 8.27 (d, 1H), 8.14 (dd, 1H), 7.53 (d, 1H), 2.87 (s, 6H) ppm. LCMS (ES) for C16H13BrN2O2: m/z 345 [M+H]$^+$, 95% pure.

Sodium 5-bromo-1-(cyclopropylamino)benzo[h]isoquinoline carboxylate (31) $^1$H NMR (400 MHz, DMSO-d6): δ 8.88 (d, 1H), 8.43 (s, 1H), 8.34 (s, 1H), 8.20 (d, 1H), 8.10 (dd, 1H), 7.33 (m, 1H), 7.31 (d, 1H), 2.85 (m, 1H), 0.75 (m, 2H), 0.66 (m, 2H) ppm. LCMS (ES) for C17H13BrN2O2: m/z 357, 359 [M+, M+2]$^+$, 95% pure.

Sodium 5-bromo-1-(methylamino)benzo[h]isoquinoline-8-carboxylate (32)$^1$H NMR (400 MHz, DMSO-d6): δ 8.93 (d, 1H), 8.44 (s, 1H), 8.36 (s, 1H), 8.17 (d, 1H), 8.14 (dd, 1H), 7.25 (d, 1H), 7.22 (m, 1H), 2.98 (d, 3H) ppm. LCMS (ES) for C15H11BrN2O2: m/z 331, 333 [M+, M+2]$^+$, 90% pure.

Synthesis of Compound 33

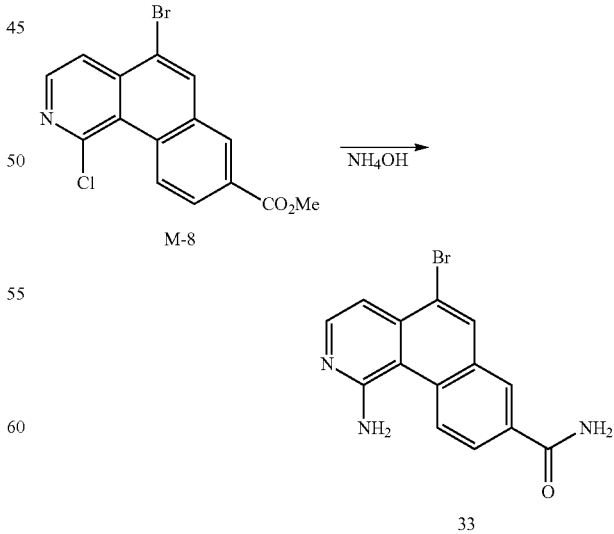

1-Amino-5-bromobenzo[h]isoquinoline-8-carboxamide (33). A mixture of M-8 (30 mg) and NH$_4$OAc (40 mg) in sealed tube was heated to 95° C. for one week. Reaction mixture was diluted with water and filter to give the crude mixture of acid and amide. The crude mixture was subjected to a reaction with NH$_4$Cl (20 mg), HATU (20 mg), DIEA (100 ul), and DMF. The resulting reaction mixture was quenched with water and filtered to give 1-Amino-5-bromobenzo[h]isoquinoline-8-carboxamide: $^1$H NMR (400 MHz, DMSO-d6): δ 9.13 (d, 1H), 8.49 (m, 2H), 8.18 (m, 2H), 8.13 (dd, 1H), 7.56 (s, 1H), 7.35 (d, 1H), 6.83 (br s, 2H) ppm. LCMS (ES) for C$_{14}$H$_{10}$BrN$_3$O: m/z 316 [M+H]$^+$.

Synthesis of Compound 34

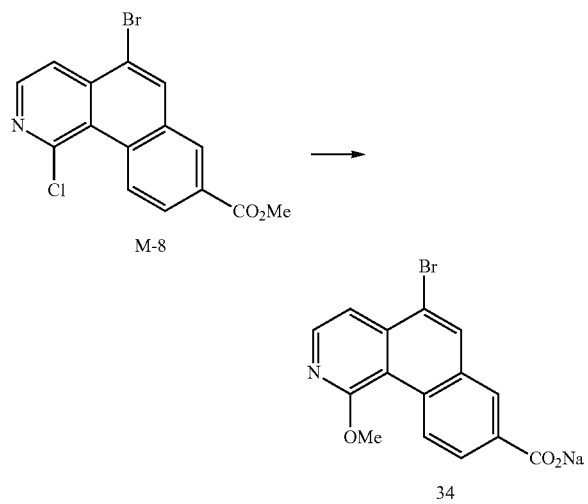

Sodium 5-bromo-1-methoxybenzo[h]isoquinoline-8-carboxylate (34): A mixture of M-8 (24 mg), LiOH hydrate (25 mg), THF (3 ml), MeOH (1 ml), and water (1 ml) was stirred at rt overnight. The reaction was concentrated, diluted with water, neutralized with acetic acid, filtered and prep (NH$_4$OAc/CH$_3$CN) purified. The acid was converted to sodium salt in a similar method of Example 1 to yield desire product: $^1$H NMR (400 MHz, DMSO-d6): δ 9.33 (d, 1H), 8.62 (s, 1H), 8.42 (s, 1H), 8.35 (d, 1H), 8.21 (dd, 1H), 7.77 (d, 1H), 4.22 (s, 3H) ppm. LCMS (ES) for C15H10BrNO3: m/z 332 [M+H]$^+$, 95% pure.

Synthesis of Compound 35

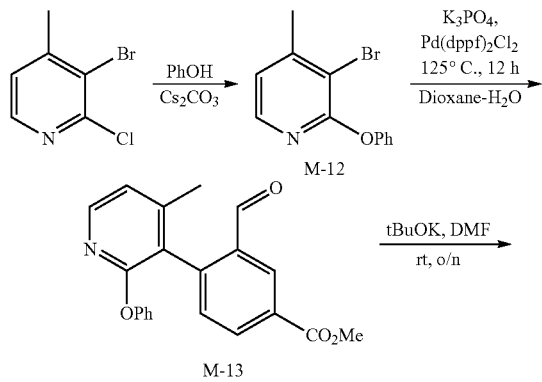

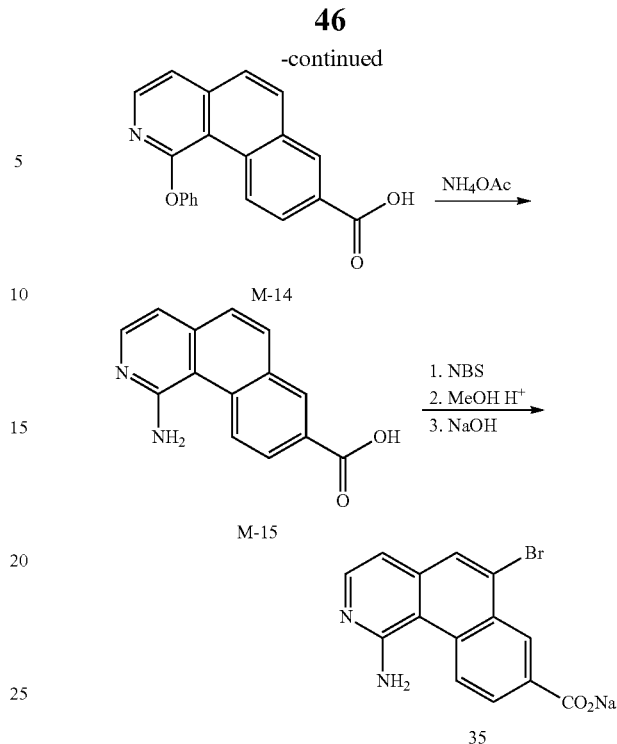

3-Bromo-4-methyl-2-phenoxypyridine (M-12). A mixture of 3-bromo-2-chloro-4-methylpyridine (320 mg, 1.546 mmol), cesium carbonate (2.05 g, 6.185 mmol) and phenol (582.1 mg, 6.185 mmol) in DMF (6 mL) was heated to 125° C. for an overnight. The resulting mixture was portioned and extracted with EtOAc. The combined organic layers were dried over MgSO$_4$, concentrated in vacuo and purification by column chromatography afforded 3-bromo-4-methyl-2-phenoxypyridine. LCMS (ES) for C$_{12}$H$_{10}$BrNO: m/z 264 [M+H]$^+$.

Methyl 3-formyl-4-(4-methyl-2-phenoxypyridin-3-yl)benzoate (M-13). A mixture of 3-bromo-2-chloro-4-methylpyridine (106.3 mg, 0.403 mmol), methyl 3-formyl-4-(4,4,5,5-tetramethyl-1,3,2-dioxaborolan-2-yl)benzoate (129 mg, 0.443 mmol), K$_3$PO$_4$ (257 mg, 1.208 mmol) and XPhos-PdG2 (32 mg, 0.04 mmol) in dioxane-water (3 mL-0.6 mL) was heated at 100° C. for 18 hours. The mixture was diluted with EtOAc (10 mL) and water (10 mL). The aqueous layer was extracted with EtOAc (20 mL×3). The combined organic layers were washed with brine, water and dried over MgSO$_4$. The mixture was filtered and concentration under reduced pressure. The crude product was then purified by column chromatography (EtOAc/Hexane) to give methyl 3-formyl-4-(4-methyl-2-phenoxypyridin yl)benzoate (866 mg). LCMS (ES) for C$_{21}$H$_{17}$NO$_4$: m/z 348.1 [M+H]$^+$.

1-Phenoxybenzo[h]isoquinoline-8-carboxylic acid (M-14). To a solution of methyl 3-formyl-4-(4-methyl-2-phenoxypyridin-3-yl)benzoate (86.6 mg, 0.249 mmol) in anhydrous DMF (1 mL) was slowly added KOtBu (56 mg, 0.499 mmol) in DMF (1 mL) under N$_2$ environment. The brown suspension was stirred for an overnight at room temperature and quenched with 1N HCl at 0° C. The resulting mixture was evaporated was purified by flash column chromatography on silica gel to yield methyl 1-phenoxybenzo[h]isoquinoline-8-carboxylate (44 mg, 47%). LCMS (ES) for C$_{21}$H$_{15}$NO$_3$: m/z 316.1 [M+H]$^+$.

1-Aminobenzo[h]isoquinoline-8-carboxylic acid (M-15). A mixture of a methyl 1-phenoxybenzo[h]isoquinoline-8- carboxylate (44 mg, 0.139 mmol) and NH$_4$OAc (400 mg) was in sealed tube and heated to 155° C. for overnight. The mixture was cooled to room temperature and dissolved in DMSO/H$_2$O. The precipitate solid was washed with water and dried overnight to give 1-aminobenzo[h]isoquinoline-8-carboxylic acid. (27.4 mg, 83%). LCMS (ES) for C$_{14}$H$_{10}$N$_2$O$_2$: m/z 239.2 [M+H]$^+$.

Sodium 1-amino-6-bromobenzo[h]isoquinoline-8-carboxylate (35): To a solution of 1-aminobenzo[h]isoquinoline-8-carboxylic acid (8.2 mg) in sulfuric acid under ice/water bath was added NBS (6.2 mg). After NBS completely dissolved the reaction mixture was placed in refrigerator (2° C.) overnight. The reaction mixture was diluted with water, quenched with NH$_4$OH and filtered. The resulting solid was refluxed in methanol with cat. Sulfuric acid overnight, and after aqueous workup, column purified to give 5 mg ester. The ester was hydrolyzed and converted to the desire sodium salt (35): $^1$H NMR (400 MHz, DMSO-d6): δ 8.92 (d, 1H), 8.35 (s, 1H), 8.10 (m, 3H), 7.78 (d, 1H), 6.65 (br s, 2H) ppm. LCMS (ES) for C14H9BrN2O2: m/z 317, 319 [M+, M+2]$^+$, 95% pure.

Example 2

HIPK2 Enzymatic Activity Inhibition: Determination of IC50 Values for Selected Compounds The half maximal inhibitory concentration (IC50) with respect to HIPK2 inhibition was determined for the compounds of the invention by using Z'-LYTE™ from ThermoFisher Scientific's SelectScreen™ Biochemical Kinase Profiling Service (Waltham, MA). Compounds were screened in 1% DMSO (final) in the well. For 10 point titrations, 3-fold serial dilutions were conducted from the starting concentration. The 2×HIPK2/Ser/Thr 09 mixture was prepared in 50 mM HEPES pH 7.5, 0.01% BRIJ-35, 10 mM MgCl$_2$, 1 mM EGTA. The black 384-well plate (Corning Cat. #4514) were used for the assay.

100 nL of 100× test compound in 100% DMSO, 2.4 uL of kinase buffer (50 mM HEPES pH 7.5, 0.01% BRIJ-35, 10 mM MgCl$_2$, 1 mM EGTA), 5 uL of 2×HIPK2/Ser/Thr 09 mixture, and 2.5 uL of 4×ATP solution were mixed and agitated for 30 seconds. Then the Kinase Reaction was incubated at room temperature for 60 minutes. The final 10 uL Kinase Reaction consisted of 3.53-19 ng HIPK2 and 2 μM Ser/Thr 09 in 50 mM HEPES pH 7.5, 0.01% BRIJ-35, 10 mM MgCl$_2$, 1 mM EGTA. After the 1 hour Kinase Reaction incubation, 5 uL of a 1:512 dilution of Development Reagent A is added. After 30 second of plate shake, the reaction plate was incubated for another 60 min at room temperature. Then the plate was read on a fluorescence plate reader (CLARIOstar, BMG Labtech, Germany) as plate reader and data was analyzed using XLfit from IDBS. The dose response curve was curve fit to model number 205 (sigmoidal dose-response model). If the bottom of the curve does not fit between −20% & 20% inhibition, it was set to 0% inhibition. If the top of the curve does not fit between 70% and 130% inhibition, it was set to 100% inhibition.

CK2 Alpha 1 Enzymatic Activity Inhibition: Determination of IC50 Values for Selected Compounds The half maximal inhibitory concentration (IC50) with respect to CK2 alpha 1 inhibition was determined for the compounds of the invention by using Z'-LYTE™ from ThermoFisher Scientific's SelectScreen™ Biochemical Kinase Profiling Service (Waltham, MA). Compounds were screened in 1% DMSO (final) in the well. For 10 point titrations, 3-fold serial dilutions were conducted from the starting concentration. The 2×CSNK2A1 (CK2 alpha 1)/Ser/Thr 11 mixture is prepared in 50 mM HEPES pH 7.5, 0.01% BRIJ-35, 10 mM MgCl2, 1 mM EGTA. The black 384-well plate (Corning Cat. #4514) were used for the assay. 100 nL of 100× test compound in 100% DMSO, 2.4 uL of kinase buffer (50 mM HEPES pH 7.5, 0.01% BRIJ-35, 10 mM MgCl$_2$, 1 mM EGTA), 5 uL of 2×CSNK2A1 (CK2 alpha 1)/Ser/Thr 11 mixture, and 2.5 uL of 4×ATP solution were mixed and agitated for 30 seconds. Then the Kinase Reaction was incubated at room temperature for 60 minutes. The final 10 uL Kinase Reaction consisted of 0.68-25.7 ng CSNK2A1 (CK2 alpha 1) and 2 μM Ser/Thr 11 in 50 mM HEPES pH 7.5, 0.01% BRIJ-35, 10 mM MgCl$_2$, 1 mM EGTA. After the 1 hour Kinase Reaction incubation, 5 uL of a 1:16 dilution of Development Reagent B is added. After 30 second of plate shake, the reaction plate was incubated for another 60 min at room temperature. Then the plate was read on a fluorescence plate reader (CLARIOstar, BMG Labtech, Germany) and data was analyzed using XLfit from IDBS. The dose response curve was curve fit to model number 205 (sigmoidal dose-response model). If the bottom of the curve does not fit between −20% & 20% inhibition, it was set to 0% inhibition. If the top of the curve does not fit between 70% and 130% inhibition, it was set to 100% inhibition.

CDK8 Enzymatic Activity Inhibition: Determination of IC50 Values for Selected Compounds The half maximal inhibitory concentration (IC50) with respect to CDK8 inhibition was determined for the compounds of the invention by using LanthaScreen™ Eu kinase binding assay from ThermoFisher Scientific's SelectScreen™ Biochemical Kinase Profiling Service (Waltham, MA). Compounds were screened in 1% DMSO (final) in the well. For 10 point titrations, 3-fold serial dilutions were conducted from the starting concentration.

The 2×CDK8/cyclinC/Eu-anti-His mixture is prepared in kinase buffer A (50 mM HEPES pH 7.5, 0.01% BRIJ-35, 10 mM MgCl$_2$, 1 mM EGTA). The Bar-coded, low volume, white 384-well plate (Greiner Cat. #784207) were used for the assay. 160 nL of 100× test compound in 100% DMSO, 3.84 uL of kinase buffer A, 8 uL of 2×CDK8/cyclinC/Eu-anti-His mixture, and 4 uL of 4× tracer 236 were mixed and shaked for 30 seconds. Then the Kinase Reaction was incubated at room temperature for 60 minutes. After the 1 hour Kinase Reaction incubation, the plate was read on a fluorescence plate reader (Infinite F500, Tecan Systems Inc, USA), and data was analyzed using XLfit from IDBS. The dose response curve was curve fit to model number 205 (sigmoidal dose-response model). If the bottom of the curve does not fit between −20% & 20% inhibition, it was set to 0% inhibition. If the top of the curve does not fit between 70% and 130% inhibition, it was set to 100% inhibition.

CDK19 (Inactive) Enzymatic Activity Inhibition: Determination of IC50 Values for Selected Compounds The half maximal inhibitory concentration (IC50) with respect to CDK19 (inactive) inhibition was determined for the compounds of the invention by using LanthaScreen™ Eu kinase binding assay from ThermoFisher Scientific's SelectScreen™ Biochemical Kinase Profiling Service (Waltham, MA). The half maximal inhibitory concentration (IC50) with respect to CDK19 (inactive) (please note that CDK19 equals CDK11) inhibition was determined for the compounds of the invention by using LanthaScreen™ Eu kinase binding assay from ThermoFisher Scientific's SelectScreen™ Biochemical Kinase Profiling Service (Waltham, MA). Compounds were screened in 1% DMSO (final) in the well. For 10 point titrations, 3-fold serial dilutions were conducted from the starting concentration.

The 2×CDK19(inactive)/Eu-anti-His mixture is prepared in kinase buffer A (50 mM HEPES pH 7.5, 0.01% BRIJ-35, 10 mM MgCl$_2$, 1 mM EGTA). The Bar-coded, low volume, white 384-well plate (Greiner Cat. #784207) were used for the assay. 160 nL of 100× test compound in 100% DMSO, 3.84 uL of kinase buffer A, 8 uL of 2×CDK19(inactive)/Eu-anti-Gst mixture, and 4 uL of 4× tracer 236 were mixed and shaked for 30 seconds. Then the Kinase Reaction was incubated at room temperature for 60 minutes. After the 1 hour Kinase Reaction incubation, the plate was read on a fluorescence plate reader (Infinite F500, Tecan Systems Inc, USA) and data was analyzed using XLfit from IDBS. The dose response curve was curve fit to model number 205 (sigmoidal dose-response model). If the bottom of the curve does not fit between −20% & 20% inhibition, it was set to 0% inhibition. If the top of the curve does not fit between 70% and 130% inhibition, it was set to 100% inhibition.

Data obtained from these assays for compounds of the invention are provided below.

| Cmpd No. | Chemical Name | HIPK2 IC50 (nM) | CK2a IC50 (nM) |
|---|---|---|---|
| 1 | Sodium 5-bromobenzo[h]isoquinoline-8-carboxylate | A | A |
| 2 | Sodium benzo[h]isoquinoline-8-carboxylate | C | A |
| 3 | Sodium 5-chlorobenzo[h]isoquinoline-8-carboxylate | B | A |
| 4 | Sodium 5-((3-chlorophenyl)amino)benzo[h]isoquinoline-8-carboxylate | B | A |
| 5 | Sodium 5-((4-chlorophenyl)amino)benzo[h]isoquinoline-8-carboxylate | B | A |
| 6 | Sodium 5-(4-chlorophenyl)benzo[h]isoquinoline-8-carboxylate | C | B |
| 7 | Sodium 5-(pyridin-3-yl)benzo[h]isoquinoline-8-carboxylate | C | A |
| 8 | Sodium 5-(pyridin-4-yl)benzo[h]isoquinoline-8-carboxylate | C | A |
| 9 | Sodium 5-methylbenzo[h]isoquinoline-8-carboxylate | B | A |
| 10 | Sodium 5-(6-aminopyridin-3-yl)benzo[h]isoquinoline-8-carboxylate | B | A |
| 11 | Sodium 5-(1H-pyrazol-3-yl)benzo[h]isoquinoline-8-carboxylate | C | A |
| 12 | Sodium 5-(cyclohexylamino)benzo[h]isoquinoline-8-carboxylate | B | A |
| 13 | (R)-5-(piperidin-3-ylamino)benzo[h]isoquinoline-8-carboxylic acid | C | C |
| 14 | (R)-5-(3-aminopiperidin-1-yl)benzo[h]isoquinoline-8-carboxylic acid | D | A |
| 15 | Sodium 5-(cyclopentylamino)benzo[h]isoquinoline-8-carboxylate | B | A |
| 16 | Sodium 5-(sec-butylamino)benzo[h]isoquinoline-8-carboxylate | B | A |
| 17 | Sodium 5-(cyclopropylamino)benzo[h]isoquinoline-8-carboxylate | A | A |
| 18 | Sodium 5-(cyclobutylamino)benzo[h]isoquinoline-8-carboxylate | B | A |
| 19 | (S)-5-(sec-butylamino)benzo[h]isoquinoline-8-carboxylic acid | C | A |
| 20 | Sodium 5-(piperidin-1-yl)benzo[h]isoquinoline-8-carboxylate | B | A |
| 21 | Sodium 5-(isopropylamino)benzo[h]isoquinoline-8-carboxylate | B | A |
| 22 | Sodium (R)-5-(sec-butylamino)benzo[h]isoquinoline-8-carboxylate | A | A |
| 23 | Sodium 5-bromo-1-chlorobenzo[h]isoquinoline-8-carboxylate | B | A |
| 24 | Sodium 5-bromo-3-chlorobenzo[h]isoquinoline-8-carboxylate | D | C |
| 25 | Sodium 1-chlorobenzo[h]isoquinoline-8-carboxylate | C | A |
| 26 | Sodium 5-nitrobenzo[h]isoquinoline-8-carboxylate | B | A |
| 27 | Sodium 5-cyanobenzo[h]isoquinoline-8-carboxylate | B | A |
| 28 | Sodium 5-cyclopropylbenzo[h]isoquinoline-8-carboxylate | B | A |
| 29 | Sodium 1-amino-5-bromobenzo[h]isoquinoline-8-carboxylate | A | A |
| 30 | Sodium 5-bromo-1-(dimethylamino)benzo[h]isoquinoline-8-carboxylate | C | C |
| 31 | Sodium 5-bromo-1-(cyclopropylamino)benzo[h]isoquinoline-8-carboxylate | C | C |
| 32 | Sodium 5-bromo-1-(methylamino)benzo[h]isoquinoline-8-carboxylate | C | B |
| 33 | 1-Amino-5-bromobenzo[h]isoquinoline-8-carboxamide | B | C |

-continued

| Cmpd No. | Chemical Name | HIPK2 IC50 (nM) | CK2a IC50 (nM) |
|---|---|---|---|
| 34 | Sodium 5-bromo-1-methoxybenzo[h]isoquinoline-8-carboxylate | C | B |
| 35 | Sodium 1-amino-6-bromobenzo[h]isoquinoline-8-carboxylate | A | B |

IC50 data for Compound 29 against CDK8 and CDK19 are A and A respectively.

wherein A: <300 nM; B: <1000 & >300 nM; C: <5000 & >1000 nM and D: >5000 nM.

Example 4

Acute Myeloid Leukemia (AML) Data
Cell Viability Method and Data:

MV-4-11 cell (ATCC CRL-9591), RS4;11 (ATCC CRL-1873) and TG-1 (ATCC CRL1608) were acquired from ATCC. MOLM14 (ACC777) was acquired from DSMZ. All cells were plated (96-well) in triplicate at 5000 cells per well for testing (n=3) with compound. On day 3, an equal volume for all wells was split-back with fresh media and compound. On day 7, the CellTiter-Glo Luminescent Cell Viability Assay (Promega) was performed to measure the response. For cell viability assay, two independent experiments have been done.

| Cell viability of compound 29 against AML cell lines (IC$_{50}$) | | | | |
|---|---|---|---|---|
| MV-4-11 | MOLM-14 | RS4;11 | TG-1 | SET-2 |
| A | A | A | A | A | wherein A: <1 μM; 1 μM < B < 10 μM

AML cancer cell lines (MV-4-11, MOLM-14, RS4;11, TG-1 and SET-2) were treated with compound 29. Compound 29 showed less than 1 μM potency in cell viability assay in all AML cell lines indicating compound 29 is effective in treating AML cancer cell lines.

Western Blot:

For cell lines: All cells were plated (6-well) at 5×10$^5$ cells per well with medium containing 1% FBS overnight. And then Compound 29 was added in different concentrations with medium containing 1% FBS. After 16 hours, cells were lysed in M-per Mammalian Protein Extraction Reagent (78501, Thermo Fisher Scientific) containing protease and phosphatase inhibitors (88669, Thermo Fisher Pierce). Total protein concentration was measured using the Pierce BCA protein Assay Kit (#23227).

For tissue: Tissue was homogenized and protein was extracted using T-per Mammalian protein extraction reagent (78510, Thermo Fisher Scientific). In the pharmacodynamics study, mice bearing tumors were treated with vehicle, 10 mg/kg, 50 mg/kg and 100 mg/kg for 6 hrs. After 6 hrs of treatment, tumors were removed for further procedure.

Figure 1B:
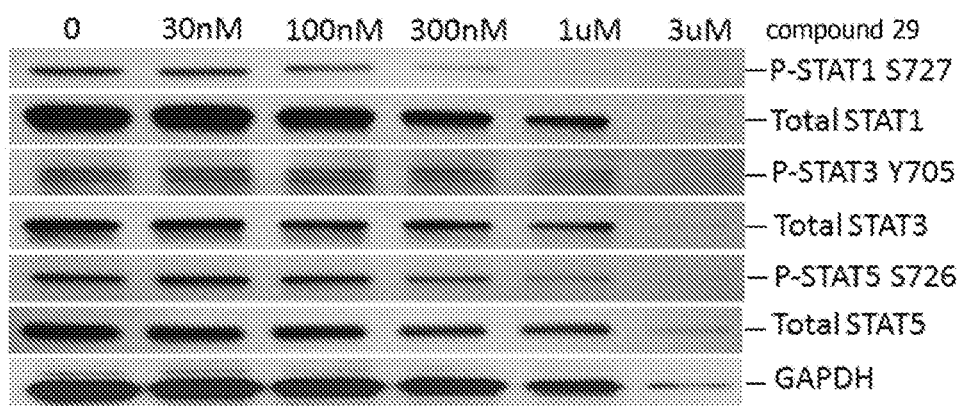
Figure 1C:
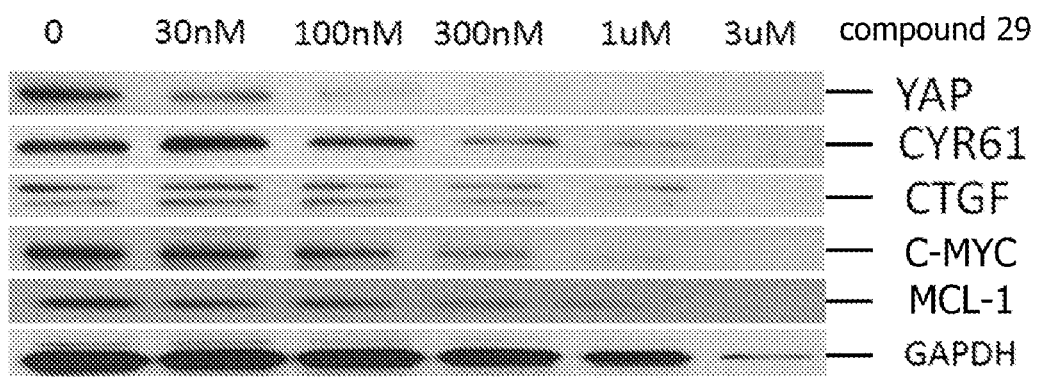
Figure 1D:
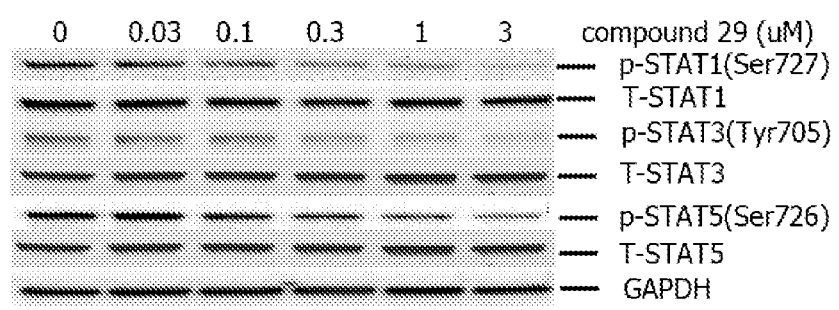
Figure 1E:
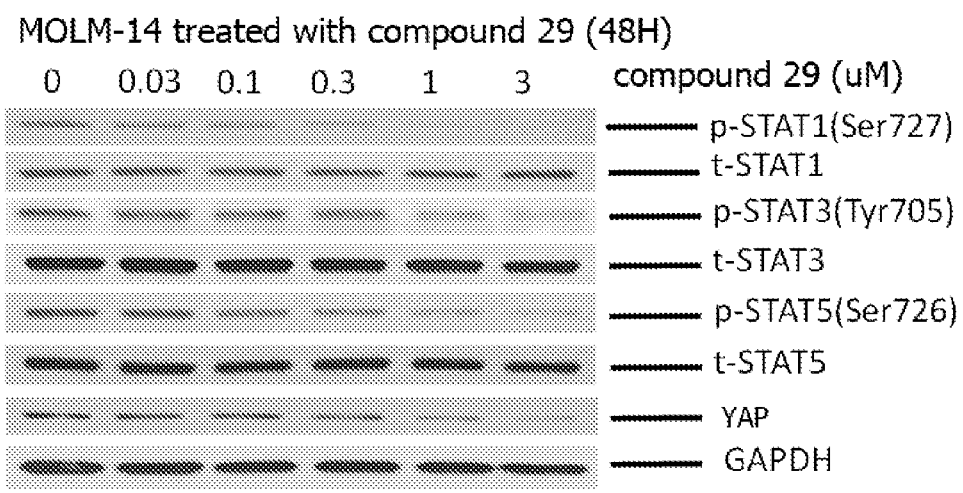

Proteins were separated on SDS-PAGE and transferred to nitrocellulose membrane. Immunoblotting were performed using specific antibodies: phosphor-Stat1-pS727 (8826, Cell signaling), total-Stat1 (14994, Cell signaling), Phospho-Stat3 (Tyr705) (9131, Cell signaling), Stat3 (9139, Cell signaling), pSTAT5-pS726 (ab128896, abcam), stat5 (94205, cell signaling), YAP (14074, Cell signaling), CYR61(14479, Cell signaling), CTGF (ab6992, Abcam), c-Myc (13987, Cell signaling), Mcl-1 (94296, Cell signaling) and GAPDH (AM4300, Invitrogen). (FIG. 1A, FIG. 1B, FIG. 1C). MV-4-11 cancer cell line was treated with compound 29 at various concentrations (30 nM up to 10 μM) for 24 hours and 48 hours, respectively. Western results of the above treatments showed the dose-response down regulation of the level of p-STAT1(Ser727), p-STAT3(Tyr705), p-STAT5(Ser726) upon treatment of compound 29 in both the 24 hour setting and 48 hour setting. Results suggest that compound 29 can down regulate the level of p-STAT1 (Ser727), p-STAT3(Tyr705) and p-STAT5(Ser726) in the dose response manner after treatment of 24 hours and 48 hours. Western results also show the dose response of the level of YAP, CYR61, CTGF, C-MYC, and MCL-1 upon treatment of compound 29 for 48 hours which suggesting compound 29 can down regulate the level of YAP, CYR61, CTGF, C-MYC, and MCL-1 in the MV-4-11 AML cancer cell line (FIG. 1D). To further prove whether compound 29 can regulate the STAT pathway and YAP, MOLM-14, another AML cancer cell line, was treated with compound 29 at various concentrations (from 30 nM up to 3 μM) for 24 hours and 48 hours, respectively. Western results of the above treatment showed dose response of the level of p-STAT1(Ser727), p-STAT3(Tyr705), p-STAT5(Ser726) and YAP upon treatment of compound 29 therefore suggesting compound 29 can down regulate p-STAT1(Ser727), p-STAT3(Tyr705) and p-STAT5(Ser726) in MOLM-14 AML cancer cell line. These results confirmed that compound 29 is effective in regulating p-STAT1, p-STAT3, p-STAT5 and YAP in AML cancer cell lines (FIG. 1E).

Example 5

Figure 2A:
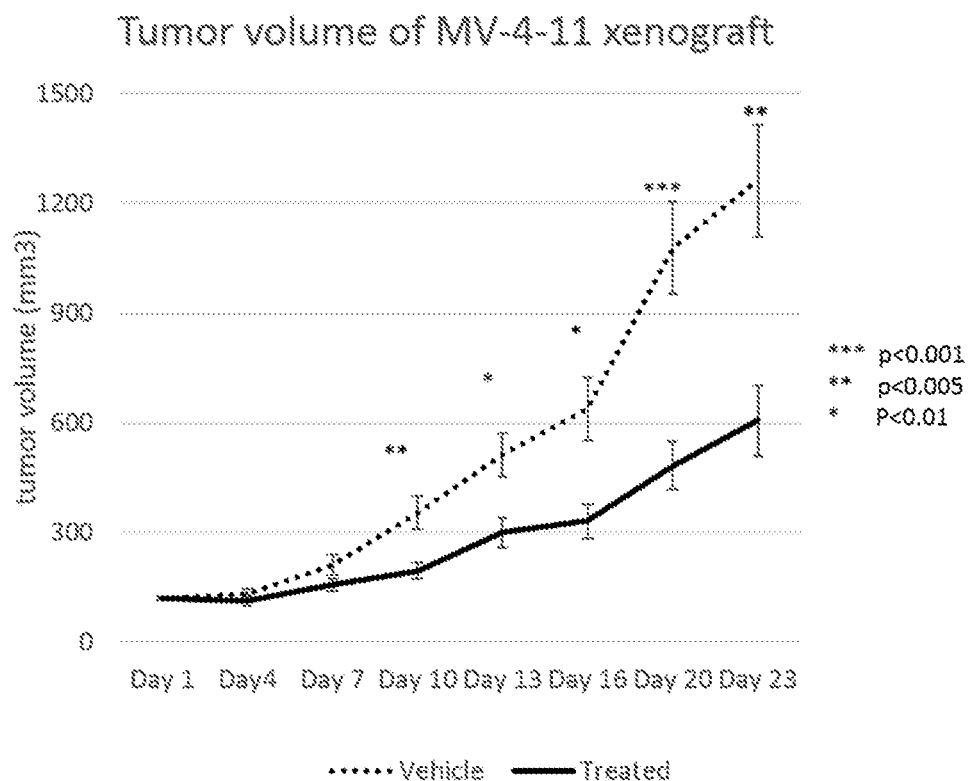
FIG. 2A-FIG. 2G: show Acute Myeloid Leukemia (AML) Data Cell viability method and data (MV-4-11 mouse xenograft model, MOLM-14 mouse xenograft model). (A) Tumor volume of MV-4-11 xenograft. (B) Body weight—MV-4-11 xenograft. (C) Tumor volume MOLM-14 xenograft, Compound 29. (D) Body weight—MOLM-14 xenograft, Compound 29. (E) Tumor weights—MOLM-14 xenograft, Compound 29. (F) MOLM-14 xenograft mouse tumor treated with Compound 29. (G) Pharmacodynamics study of MOLM-14 xenograft treated with Compound 29.
Figure 2B:
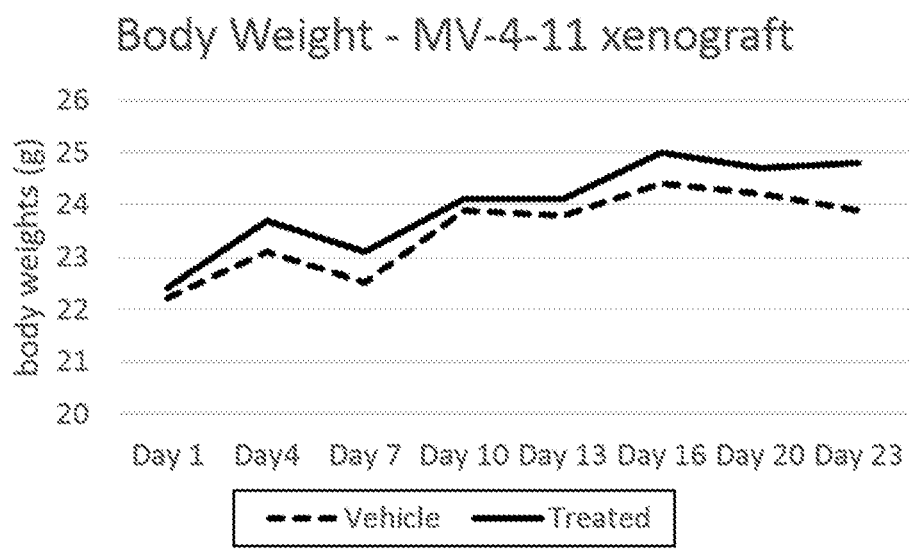
Figure 2C:
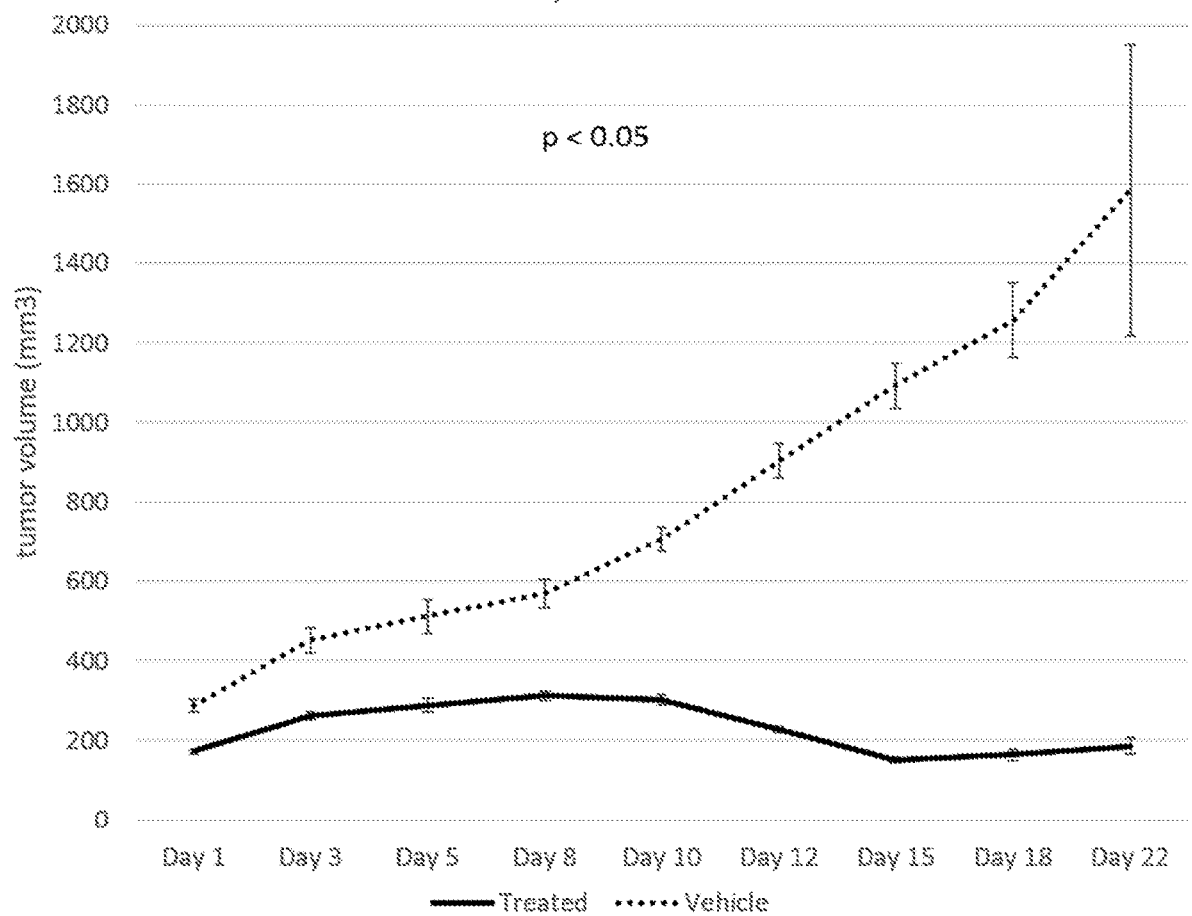
Figure 2D:
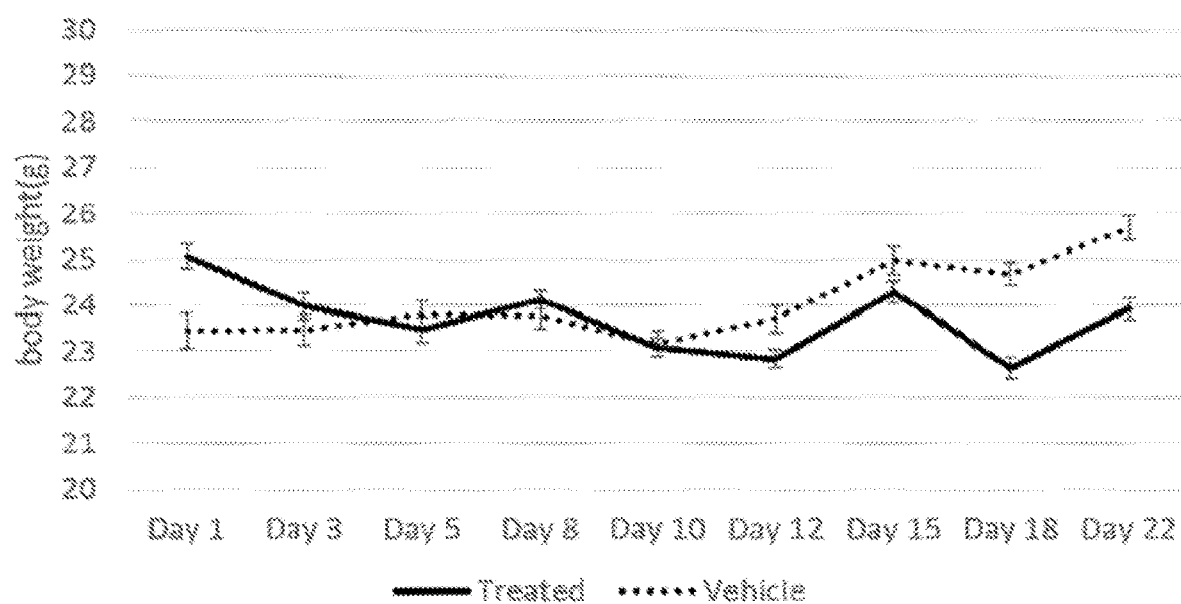
Figure 2E:
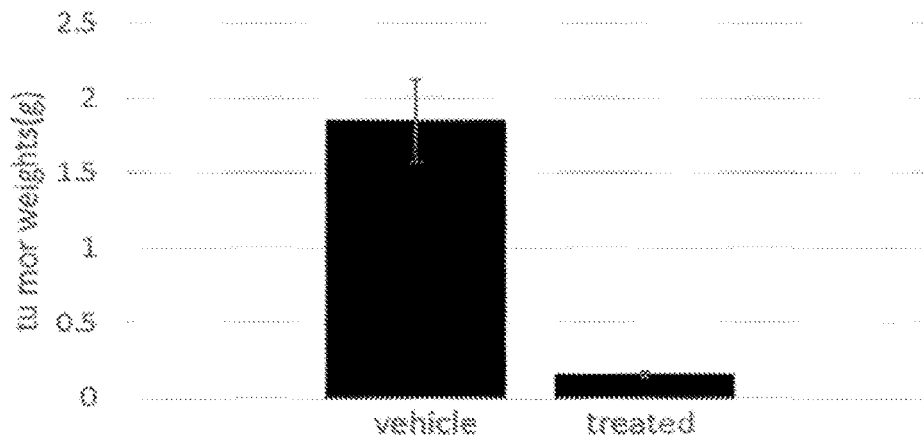
Figure 2F:
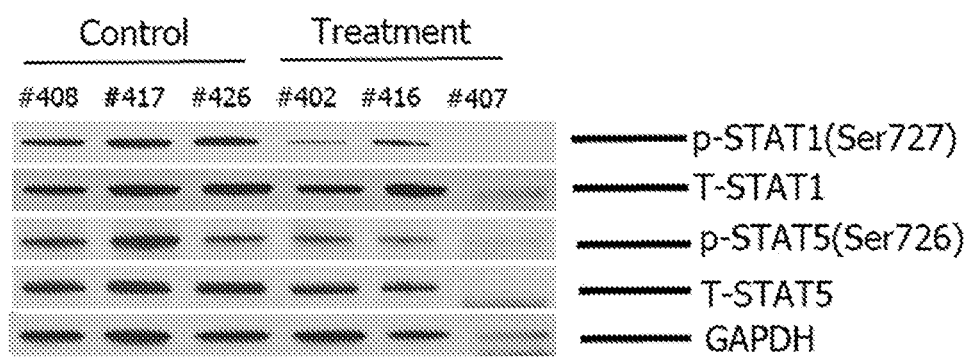
Figure 2G:
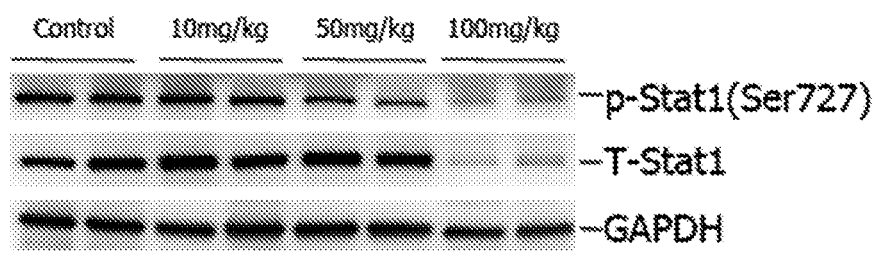

MV-4-11 Mouse Xenograft Model (FIG. 2A-2B):

40 CR female NCr nu/nu mice (Charles River Laboratories) were injected with 1×10$^7$ MV-4-11 cells in 50% matrigel s.c. in flank. Cell Injection Volume is 0.1 mL/mouse for MV-4-11 cells. Age of mice at start date is 8 to 12 weeks. Perform a pair match when tumors grow after two weeks and begin treatment. Compound 29 was given orally twice a day for 21 consecutive days. Body weight and tumor size were measured every three days.

In the MV-4-11 xenograft model, mice were treated with compound 29 with 50 mg/kg for 21 days (orally, b.i.d). The tumor volume from control and vehicle group were measured, compared. Statistical significance was calculated and showed in the graph. Tumors from the treated group are smaller compared that from the control group to a different extent at each measuring time point and reached only about half the size of tumors from the control group at the last measurement point. The graph of tumor volume proved that compound 29 is effective in inhibiting the growth of tumor in the MV-4-11 xenograft model. Body weights of mice in both groups were measured and plotted. Data suggest that during 21 days of treatment, mice didn't suffer from weight loss therefore indicating compound 29 is well tolerated in the treated mice. These two set of data taken together demonstrated compound 29 is effective for the MV-4-11 AML xenograft model.

MOLM-14 Mouse Xenograft Model (FIG. 2C, 2D, 2E, 2F, 2G):

40 athymic nude mice (Taconic Biosciences) were injected with $5 \times 10^6$ MOLM-14 cells in 50% matrigel s.c. in flank. Cell Injection Volume is 0.2 ml/mouse for MOLM-14. Age of mice at start date is 12-14 weeks. Perform a pair match when tumors grows after two weeks and begin treatment. Compound 29 was dissolved in saline and was given orally twice a day on a schedule of five days on/two days off for three weeks. Body weight and tumor size were measured every other day when mice being treated. After the last administration, mice were euthanized for tumor collection.

To further prove the efficacy of compound 29 in AML xenograft model, we took another model, MOLM-14 xenograft model. In the MOLM-14 xenograft model, mice were treated with compound 29 at 50 mg/kg for 21 days (orally, b.i.d). The tumor volume from control and vehicle group was measured. Statistical significance was calculated and showed in the graph. With tumors from control group continue to grow quickly in the 21 days of experiment, growth of tumors from treated group was greatly inhibited by compound 29. The graph of tumor volume proved the efficacy of compound 29 in the MOLM-14 xenograft model. Body weights of mice in both groups were measured and plotted. Data suggest that during treatment, mice from the treatment group only suffered from acceptable weight loss (<5%) indicating compound 29 is well tolerated by the treated mice. These two sets of data together demonstrated compound 29 is effective not only for MV-4-11 AML xenograft model but also for MOLM-14 AML xenograft model.

Tumors from the MOLM-14 xenograft study were collected and processed for western analysis. In the western results showing above, the level of p-STAT1 (Ser727) in the three mice samples from the treated group were much lower compared to that in the three mice samples from the control group. The same phenomenon was observed for the level of p-STAT5(Ser726) in which the treated group showed lower level of p-STAT5. These results suggest that treatment of compound 29 can down regulate the levels of p-STAT1 (Ser727) and p-STAT(Ser726) in vivo and can explain the efficacy of compound 29 in MOLM-14 AML xenograft study is through the STAT pathway.

In the pharmacodynamics study of MOLM-14 xenograft study treated with compound 29, a dose response (10 mg/kg, 50 mg/kg and 100 mg/kg) of down regulation of p-STAT1 (Ser727) was observed. The western results here suggest that in the in vivo study, compound 29 can also down regulate the level of p-STAT1 (Ser727) in a dose response manner. This proved that compound 29 can down regulate the STAT pathway in vivo in the AML xenograft model.

Example 6

Acute Lymphoblastic Leukemia, Colon Cancer, Breast Cancer, Cervical Cancer, Mesothelioma and Lung Cancer Data Cell Viability Assay CLL-119, Hela, HCT116, MCF7, Colo205, SW620, H2052, MSTO-211H, U-251, Colo 357, OE33, Huh-7, A549, BT474, A204 and H290 cells were acquired from UCSF Cell and Genome Engineering Core. A549-Brm3 and H2030-Brm3 were from UCSF thoracic oncology lab. All cells were plated (96-well) in triplicate at 500 cells per well for testing (n=3) with compound. Medium was changed once on day 3. On day 7, the CellTiter-Glo Luminescent Cell Viability Assay (Promega) was performed to measure the response. For cell viability assay, two independent experiments have been done.

| Cell viability of compound 29 against various cancer cell lines ($IC_{50}$) | | | | | | | | |
|---|---|---|---|---|---|---|---|---|
| CLL-119 | HCT116 | Colo205 | SW620 | Hela | MCF7 | H2052 | H2030-BRM3 | A549 |
| A | B | A | B | B | B | B | A | B |

| A549-BRM3 | OE33 | U-251 | Colo357 | Huh-7 | MSTO-211H | H290 | A204 | BT474 |
|---|---|---|---|---|---|---|---|---|
| B | A | B | B | A | B | B | B | B | wherein A: <1 µM; 1 µM < B < 10 µM

Cell viability data of compound 29 proved that compound 29 is effective in inhibiting the growth of various cancer cell lines including acute lymphoblastic leukemia (CLL-119), colon cancer (HCT116, colo205, SW620), cervical cancer (Hela), breast cancer (MCF7, BT474), mesothelioma (H2052, H290, MSTO-211H), liver cancer (Huh-7), esophageal carcinoma (OE33), glioblastoma (U-251), pancreatic cancer (Colo 357), sarcoma (A204) and lung cancer (A549, A549-brm3, H2030-brm3).

Example 7

Synergy of Compound 29 with Glycolysis Inhibitors in Colon Cancer, Breast Cancer, Cervical Cancer and Lung Cancer Method of Synergy Experiment of Compound 29 and 2DG:

SW620 cells were plated (96-well) in triplicate at 500 cells per well for testing (n=3) with 5 mM 2-DG and different concentrations of compound 29 (0-10 uM). Medium was changed once on day 3. On day 7, the CellTiter-Glo Luminescent Cell Viability Assay (Promega) was performed to measure the response. For cell viability assay, two independent experiments have been done.

| Compound 29 synergizes with 2DG in colorectal cancer cell line SW620 | |
|---|---|
| Compound 29 + 5 Mm 2DG | Compound 29 |
| A | B | wherein A: <1 µM; 1 µM < B < 10 µM

One of the hallmarks of cancer is its aerobic glycolysis (i.e., Warburg effect). CDK8 kinase is required for the transcription of multiple genes (e.g., GLUT1) required for the glucose metabolism. Inhibition of CDK8 impairs reduces glucose uptake and glycolysis and sensitizes cancer cells to glycolysis inhibitors such as the glucose analog 2-deoxy-Dglucose (2DG). Compound 29 synergizes with 2DG in the viability assay of colorectal cancer cell line SW620. Combination treatment with 2DG further decreased viability confirming that Compound 29 can enhance the effects of 2DG on cancer cells. These results indicate that Compound 29 and pharmacological inhibition of glycolysis may be an effective strategy for targeting colorectal cancer and other tumor types such as lung cancer and mesothelioma.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or a salt or a hydrate or a solvate thereof, having a structure according to formula (I):

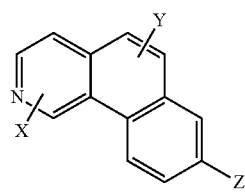
(I)

wherein Z is —COOR$^5$ or —C(O)NHR$^5$, wherein R$^5$ is H or substituted or unsubstituted alkyl or substituted or unsubstituted cycloalkyl;

Y is H or halogen or nitro or cyano or substituted or unsubstituted aryl or substituted or unsubstituted heteroaryl or substituted or unsubstituted alkyl or substituted or unsubstituted cycloalkyl or NR$^1$R$^2$, wherein R$^1$ and R$^2$ are each independently selected from H or substituted or unsubstituted alkyl or substituted or unsubstituted cycloalkyl or substituted or unsubstituted heterocycloalkyl or halosubstituted aryl or wherein R$^1$ and R$^2$, along with the nitrogen to which they are attached, are optionally joined to form a substituted or unsubstituted 4 to 8 membered ring; and X is H or halogen or OR$^3$ or NR$^3$R$^4$, wherein R$^3$ and R$^4$ are each independently selected from H or substituted or unsubstituted alkyl or substituted or unsubstituted cycloalkyl or wherein R$^3$ and R$^4$, along with the nitrogen to which they are attached, are optionally joined to form a substituted or unsubstituted 4 to 8 membered ring.

2. The compound of claim 1, or a salt or a hydrate or a solvate thereof, having a structure which is

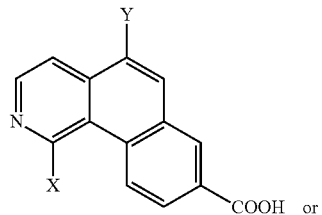
(VIa)

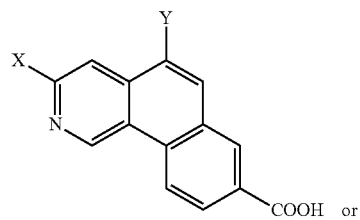
(VIb)

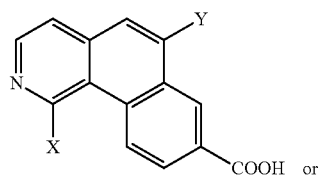
(VIc)

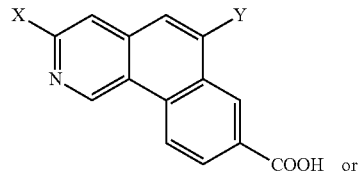
(VId)

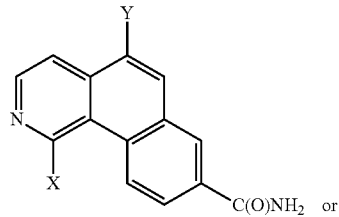
(VIIa)

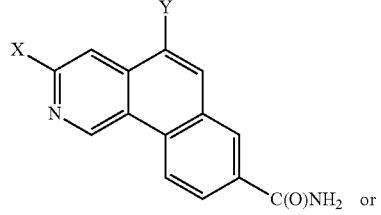
(VIIb)

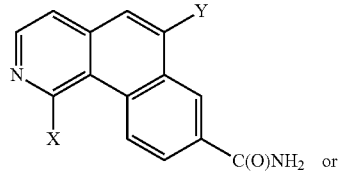
(VIIc)

-continued

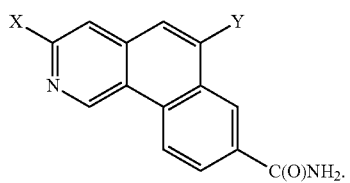
(VIId)

3. The compound of claim 1, or a salt or a hydrate or a solvate thereof, having a structure which is

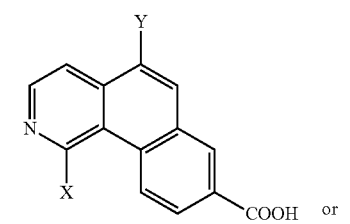
(VIa)

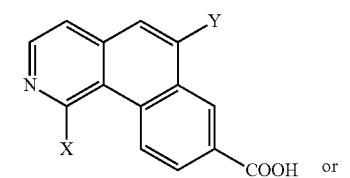
(VIc)

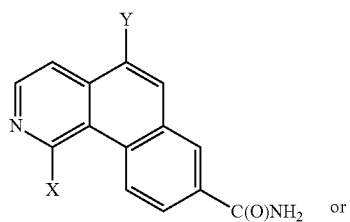
(VIIa)

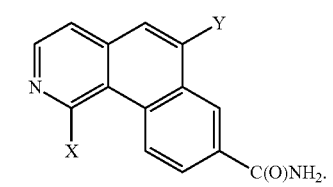
(VIIc)

4. The compound of claim 1, or a salt or a hydrate or a solvate thereof, wherein X is H or NR³R⁴.

5. The compound of claim 1, or a salt or a hydrate or a solvate thereof, wherein X is H or NH₂.

6. The compound of claim 1, or a salt or a hydrate or a solvate thereof, wherein Y is halogen or unsubstituted alkyl or NR¹R².

7. The compound of claim 1, or a salt or a hydrate or a solvate thereof, wherein Y is Br or Cl or CH₃ or amino substituted pyridine.

8. The compound of claim 1, or a salt or a hydrate or a solvate thereof, wherein the compound is

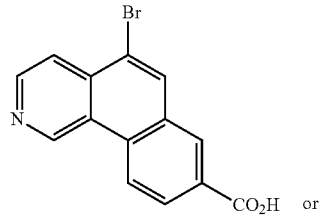 or

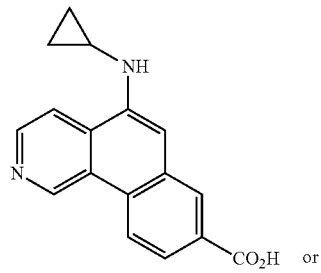 or

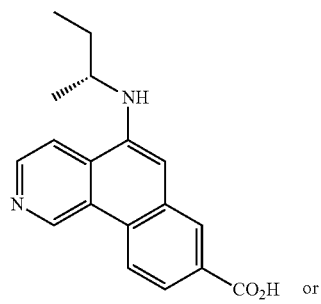 or

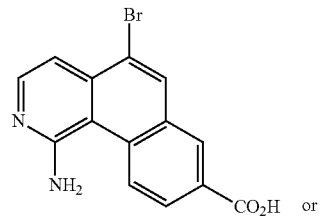 or

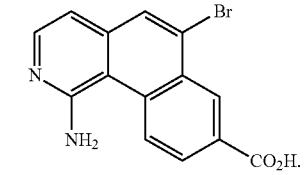.

9. The compound according to claim 1, or a salt or a hydrate or a solvate thereof, having a structure selected from the group consisting of:

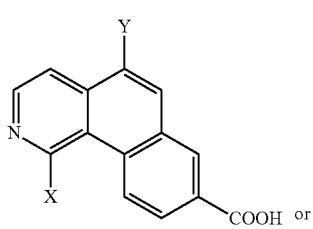
(VIa)

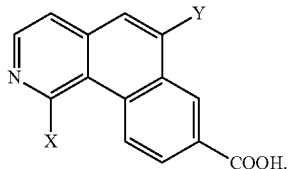
(VIc)

10. The compound according to claim 1, or a salt or a hydrate or a solvate thereof, having a structure selected from the group consisting of:

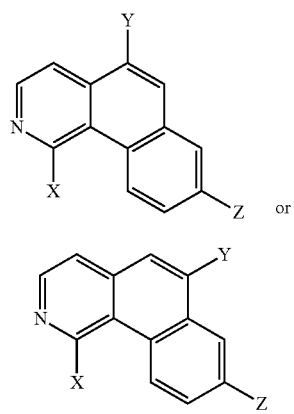
(Va) or (Vc)

wherein Y is Br or Cl or CN or NO₂ or unsubstituted C₁ or C₂ or C₃ or C₄ alkyl or p-halophenyl- or m-halophenyl or o-halophenyl or pyridinyl or aminopyridinyl or pyrazolyl or methyl or phenyl or p-chlorophenyl or cyclopropyl or pyridin-3-yl or 6-amino pyridin-3-yl or pyridin-4-yl or pyrazol-3-yl.

11. The compound according to claim 1, or a salt or a hydrate or a solvate thereof, having a structure selected from the group consisting of:

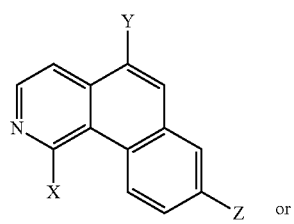
(Va) or

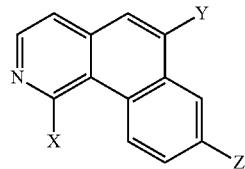
(Vc)

wherein Z is —COOH or —CONH₂, and Y is halogen or cyano or nitro or methyl or phenyl or halogen substituted phenyl or cyclopropyl or piperidine or amino substituted piperidine or pyridinyl or pyrazole.

12. A compound, or a salt or a hydrate or a solvate thereof, having a structure selected from the group consisting of:

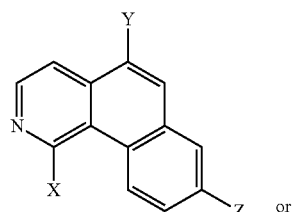
(Va) or (Vc)

wherein Z is —COOH or —CONH₂, X is H or NH₂, and Y is halogen or cyano or nitro or methyl or phenyl or halogen substituted phenyl or cyclopropyl or piperidine or amino substituted piperidine or pyridinyl or pyrazole.

13. A compound, or a salt or a hydrate or a solvate thereof, having a structure selected from the group consisting of: 5-bromobenzo[h]isoquinoline-8-carboxylate, 5-chlorobenzo[h]isoquinoline-8-carboxylate, 5-methylbenzo[h]isoquinoline-8-carboxylate, 5-(cyclohexylamino)benzo[h]isoquinoline-8-carboxylate, 5-(sec-butylamino)benzo[h]isoquinoline-8-carboxylate, 5-(cyclopropylamino)benzo[h]isoquinoline-8-carboxylate, 5-(cyclobutylamino)benzo[h]isoquinoline-8-carboxylate, 5-cyanobenzo[h]isoquinoline-8-carboxylate, 5-cyclopropylbenzo[h]isoquinoline-8-carboxylate, 1-amino-5-bromobenzo[h]isoquinoline-8-carboxylate, 5-bromo-1-methoxybenzo[h]isoquinoline-8-carboxylate, and 1-amino-6-bromobenzo[h]isoquinoline-8-carboxylate.

* * * * *